(12) United States Patent
Suzuki et al.

(10) Patent No.: US 6,242,430 B1
(45) Date of Patent: Jun. 5, 2001

(54) CYCLODEXTRIN-BASED ROTAXANE DYES, LABELING AGENT USING THE DYE, AND A METHOD FOR LABELING

(75) Inventors: Tomomi Suzuki, Hamakita; Hitoshi Nohta, Fukuoka; Shigetoshi Okazaki, Hamakita, all of (JP)

(73) Assignee: Laboratory of Molecular Biophotonics, Hamakita (JP)

( * ) Notice: Subject to any disclaimer, the term of this patent is extended or adjusted under 35 U.S.C. 154(b) by 0 days.

(21) Appl. No.: 09/301,635

(22) Filed: Apr. 29, 1999

(30) Foreign Application Priority Data

Apr. 30, 1998 (JP) .................................................. 10-121255

(51) Int. Cl.⁷ ............................. A61K 31/20; C07M 1/00
(52) U.S. Cl. ............................................ 514/58; 536/103
(58) Field of Search ................................ 574/59; 514/58; 536/103

(56) References Cited

FOREIGN PATENT DOCUMENTS

| | | |
|---|---|---|
| 9-216815 | 8/1997 | (JP) . |
| 9-301893 | 11/1997 | (JP) . |
| WO 90/02141 | 3/1990 | (WO) . |
| WO 98/26287 | 6/1998 | (WO) . |

OTHER PUBLICATIONS

Anderson et al., *Angew Chem. Int. Ed. Engl.*, 36(12), 1310–1313 (1997).
Kunitake et al., *Chemistry Letters*, 6, 1033–1036 (1993).
Toki et al., *Bull. Chem. Soc. Jpn.*, 66(11), 3382–3386 (1993).
Yamanari et al., *Bull. Chem. Soc. Jpn.*, 57(6), 1596–1603 (1984).
Isnin et al., *J. Am. Chem. Soc.*, 113(21), 8188–8190 (1991).
Ogino, *J. Am. Chem. Soc.*, 103(5), 1303–1304 (1981).
Tamura et al., *Chem. Lett.*, 369–370 (1998).
Wylie et al., *J. Am. Chem. Soc.*, 114(8), 3136–3138 (1992).
Yamanari et al., *Bull. Chem. Soc. Jpn.*, 56(8), 2283–2289 (1983).

*Primary Examiner*—Elli Peselev
(74) *Attorney, Agent, or Firm*—Leydig, Voit & Mayer, Ltd.

(57) ABSTRACT

This invention provides rotaxane type dyes. Specifically, the rotaxane type dye according to the invention has a rotaxane structure which binds dye molecules to both of the termini of a chain group penetrating a cyclodextrin ring, which possesses excellent water-solubility, and which is capable of having a plurality of different dyes.

12 Claims, 22 Drawing Sheets

(TAMRA) —don— (TAMRA)—CD ROTAXANE (TAMRA) —don— (TAMRA)

(FAM) — don — (FAM) — CD ROTAXANE (FAM) — don — (FAM)

(FAM) — don — (TAMRA) — CD ROTAXANE (FAM) — don — (TAMRA)

(FAM) — don — (Cy5) — CD ROTAXANE (FAM) — don — (Cy5)

(FAM) — don — (TAMRA) — CDcooh ROTAXANE

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Biologically active peptide

<400> SEQUENCE: 1

Gly Cys Asp Arg Val Tyr Ile His Pro Phe
                 5                  10

CYCLODEXTRIN-BASED ROTAXANE DYES, LABELING AGENT USING THE DYE, AND A METHOD FOR LABELING

BACKGROUND OF THE INVENTION

1. Field of the Invention

This invention relates to a novel dye having a rotaxane type structure with cyclodextrin, a labeling agent using the dye, and a labeling method using the agent.

2. Related Background Art

In the field of bioscience, including genetic engineering, one of the most commonly employed analytical methods among those for detecting various substances or those for labeling specified substances is the method relying on dyes: particularly, fluorometric analysis relying on fluorescent dyes. To such end, there have been developed and used labeling agents that rely on dyes having a variety of properties, particularly fluorescent dyes.

However, problems existed: (1) A problem that dyes known in the art or labeling agents using the same were not adequate in their water-solubility; (2) A further problem that there was no availability for labeling agents which rely on dyes of the multi-wavelength type capable of conforming to multiple coloration—a strong demand in recent years—as well as for labeling methods using the aforementioned agents.

SUMMARY OF THE INVENTION

It is an objective of this invention to provide a dye displaying excellent water-solubility and capable of multiple coloration. Further, it is another objective of the invention to provide a labeling agent containing such dye, as well as a labeling method relaying on said labeling agent.

The present inventors made thorough investigations in an effort to solve the drawbacks encountered in the prior art as described above, and have discovered that by making a dye, which is water-insoluble or sparingly water-soluble, into a rotaxane structure combined with cyclodextrin (water-soluble), one can obtain a dye of the multi-wavelength type that is excellent in water-solubility and, in addition, that is capable of conforming to multiple coloration. It has also been discovered that one can obtain a labeling agent containing such dye that has a rotaxane structure. Furthermore, a labeling method using said labeling agent has been developed.

Particularly, it has been discovered that when said dye is a fluorescent dye, it leads to a fluorescent dye of the mutli-wavelength type which possesses excellent water-solubility and, in addition, which is capable of conforming to multiple coloration, to a labeling agent containing this fluorescent dye, and further to a labeling method using this labeling agent; thus, this invention has been accomplished.

Specifically, the structure of a rotaxane type dye according to this invention is based on that which (1) combines a dye molecule with cyclodextrin and which (2) links the dye molecule to at least one terminus of a chain group penetrating said cyclodextrin ring. Therefore, the dye having such cyclodextrin-rotaxane structure possesses excellent water-solubility, because it is provided with cyclodextrin. Further, it is possible that the dye has a structure which links dye molecules to both termini of the chain group penetrating the cyclodextrin ring. In this case, it becomes also possible to bind not only the same kind of dye but also different kinds of dye.

In addition, the dye according to the invention can be made into a labeling agent for labeling various substances in aqueous solution by the introduction of various functional groups the dye molecule itself has or by the introduction of various reactive groups. The dyes according to the invention encompass both those having fluorescent nature and those having no fluorescent nature.

More specifically, the dye according to the invention is one that is characterized by a rotaxane type wherein a dye is bound to at least one terminus of a chain group and the chain group penetrates a cyclodextrin ring.

Further, the dye according to the invention is a rotaxane type dye represented by the following formula 1:

(Formula 1)

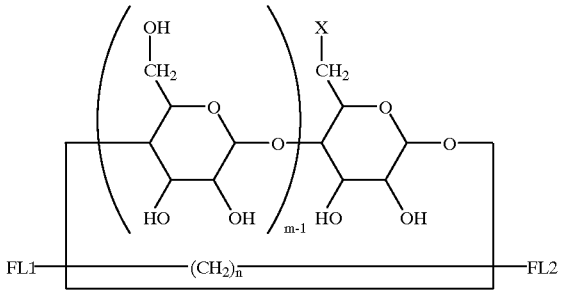

wherein each of FL1 and FL2 represents a dye; n represents an integer of 8–12; m represents an integer of 6–8; and X represents any one of OH, Cl, Br, I, $NH_2$, NCO, NHCO, and $(CH_2)_3CO_2H$.

Also, the dye according to the invention is a rotaxane type dye represented by the following formula 2:

(Formula 2)

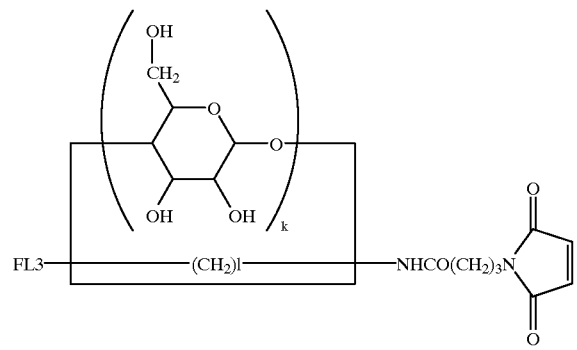

wherein FL3 represents a dye; k represents an integer of 6–8; and l represents an integer of 8–12.

Further, the dye according to the invention is a rotaxane type dye wherein the dye is a fluorescent dye.

In addition, the labeling agent according to the invention is one that is characterized by the use of the dye as described above.

Furthermore, the labeling method according to the invention is one that is characterized by the use of the labeling agent as described above.

Since the rotaxane type dye according to the invention has a rotaxane structure which binds dye molecules to both of the termini of a chain group penetrating a cyclodextrin ring, it is the one that can possess excellent water-solubility and can be provided with plural different dyes.

Still further, with the use of various bonding groups for labeling reaction that are contained in the dye molecules, CD, or chain group of the rotaxane type dye according to the invention, it becomes possible to label various substances under aqueous solution conditions.

This invention will be explained in more detail based on embodiment hereinbelow.

DESCRIPTION OF THE PREFERRED EMBODIMENTS

Figure 1A:
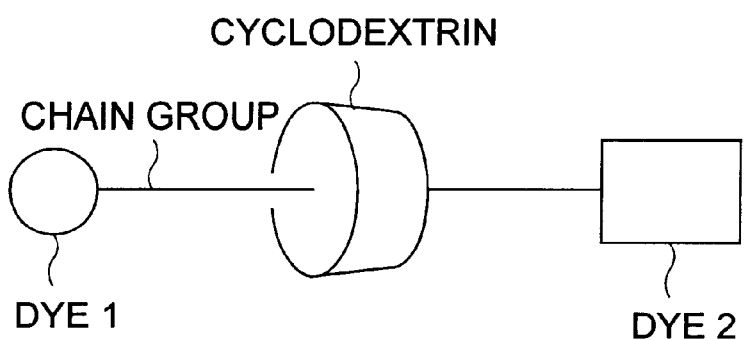
FIG. 1A is a schematic illustration of one of the basic structures of the rotaxane type dye according to this invention.

As FIG. 1A schematically shows, one of the basic structures of the rotaxane type dye according to this invention is characterized by a rotaxane structure which binds dye molecules (represented by Dyes 1 and 2 in the figure) to both of the termini of a chain group penetrating CD.

Figure 1B:
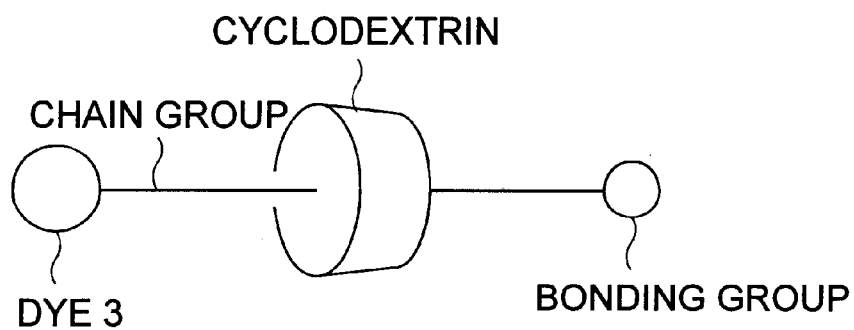
FIG. 1B is a schematic illustration of another of the basic structures of the rotaxane type dye according to the invention.

As FIG. 1B schematically shows, another basic structure is characterized by a rotaxane structure which binds a dye molecule (represented by Dye 3 in the figure) to one terminus of a chain group penetrating CD as well as binds a reactive group to the other terminus.

Since the molecular size of Dyes 1, 2 or 3 is sufficiently large, each dye can not possibly be dislocated from the cyclodextrin ring. Although said chain group penetrates the cyclodextrin ring, its molecular motion is relatively possible within cyclodextrin depending on the kind of said chain group.

The rotaxane type dyes according to the invention prove to display adequate water-solubility due to the contribution of large hydrophilicity of the cyclodextrin ring even if the dye molecules contained therein (Dyes 1–3 in the figures) are water-insoluble or sparingly soluble. Besides, they prove to be able to exist very stably in ordinary labeling reactions or under a variety of measuring conditions subsequent thereto.

The rotaxane type dyes according to this invention will be explained in more detail hereinbelow.

1. Cyclodextrin (abbreviated as "CD" hereinbelow)

(1) The kind of CD to be used in the rotaxane type dyes according to the invention is not particularly limited. It may be such that the hydrophobic space within the CD has the size sufficient to let the chain group (which will be described below) penetrate. Concretely, the number of glucose is preferably six or more when the chain group is methylene, although it depends on the kind of the chain group.

Such CDs, which can be used in the invention, may be obtained for use from those that are commercially available as a variety of cyclodextrins. Namely, depending on the number of glucose, α-cyclodextrin, β-cyclodextrin, or γ-cyclodextrin is available in high purity. Thus, these and cyclodextrin derivatives having structures analogous to these can preferably be used as CDs of the invention. Specifically, the following are preferably usable:

α-cyclodextrin, β-cyclodextrin, or γ-cyclodextrin; glucosyl-α-cyclodextrin, glucosyl-β-cyclodextrin, glucosyl-γ-cyclodextrin, mantosyl-α-cyclodextrin, mantosyl-β-cyclodextrin, mantosyl-γ-cyclodextrin, or the like (the foregoing have branched structures); 6-O-methyl-α-cyclodextrin, 6-O-methyl-β-cyclodextrin, 6-O-methyl-γ-cyclodextrin, 2,6-di-O-methyl-α-cyclodextrin, 2,6-di-O-β-cyclodextrin, 2,6-di-O-methyl-γ-cyclodextrin, or 2,3,6-tri-O-methyl-α-cyclodextrin, 2,6-di-O-ethyl-α-cyclodextrin, 2,3,6-tri-O-ethyl-α-cyclodextrin or the corresponding β-cyclodextrins and γ-cyclodextrins (the foregoing are alkylated cyclodextrin derivatives); and 2-hydroxyethyl-α-cyclodextrin, 2-hydroxypropyl-α-cyclodextrin, 3-hydroxypropyl-α-cyclodextrin, 2,3-dihydroxypropyl-α-cyclodextrin, 2,3,6-tri-O-acyl(C2–C18)-α-cyclodextrin, O-carboxylmethyl-O-ethyl-α-cyclodextrin, α-cyclodextrin sulfate, α-cyclodextrin phosphate, or the like and the corresponding β-cyclodextrins and γ-cyclodextrins, etc. (Kaneto Uegama, Abstracts of the 12th Cyclodextrin Symposium, 1 (1993).)

In addition, cyclodextrin oligomers and polymers having various molecular weights are commercially available and they can be utilized.

Figure 2A:
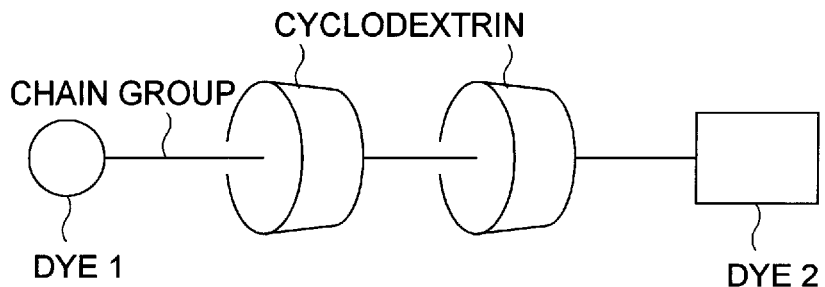
FIG. 2A is an illustration of some structures of the rotaxane type according to the invention.
Figure 2B:
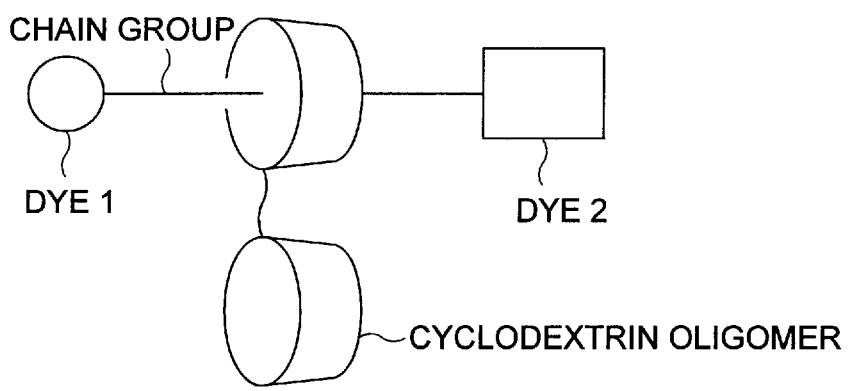
FIG. 2B is an illustration of some structures of the rotaxane type according to the invention.
Figure 2C:
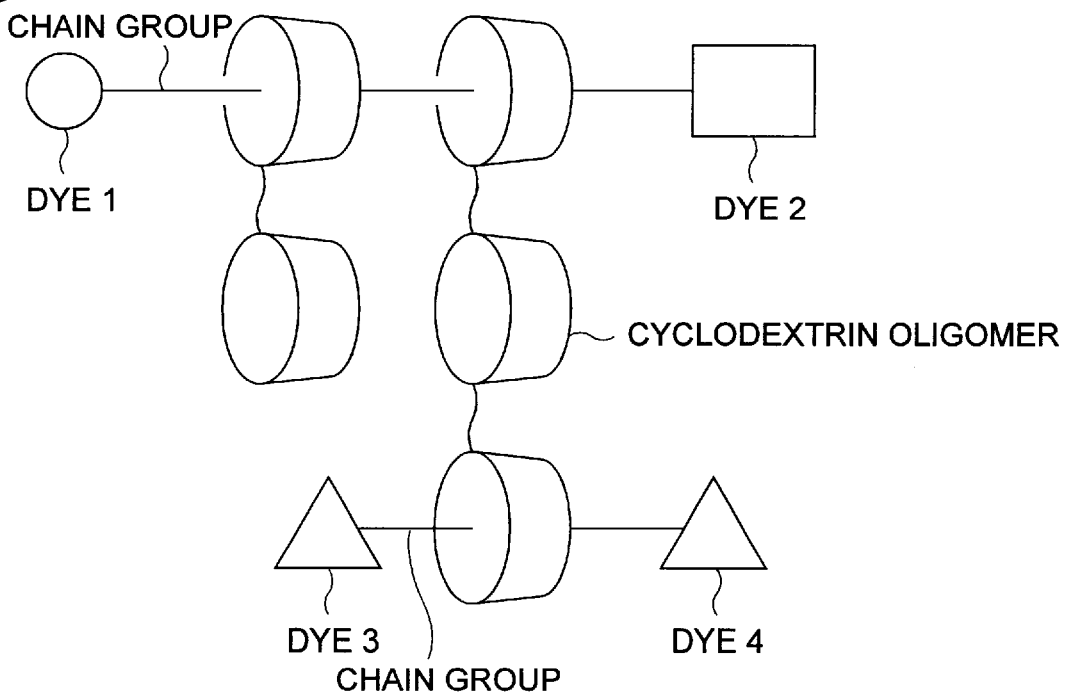
FIG. 2C is an illustration of some structures of the rotaxane type according to the invention.

(2) There is no particular limitation to the number of CD the rotaxane dye according to the invention has. FIGS. 2A–2C show embodiments of CD that can preferably be used in the invention. The embodiment of A in the figure shows one in which two or more CDs in series penetrate the chain group. Also, B shows an embodiment where such two or more CDs are bound. Further, the two or more CDs do not necessarily need to be the same kind.

When plural CDs are contained, an embodiment having plural chain groups (which are further provided with dye molecules at both of their termini) is also possible, and one such example is shown in FIG. 2C.

(3) Cyclodextrin Having an Activated Group Introduced Thereinto

Hydroxyl groups CD has can preferably be utilized as activated groups for labeling specified substances by the use of a rotaxane type dye according to the invention; but the invention further embraces those where suitable activated groups are introduced into CD. Specifically, one or more hydroxyl groups of CD are easily converted to carboxyl, halogen, amino, or isocyanate groups.

In addition, it is possible that said reactive group is bound for use to one terminus of the chain group: one such example is shown in FIG. 1B.

2. Chain Group (1) The chain group that a rotaxane type dye according to the invention has is not particularly limited insofar as it can allow dye molecules to be bound to both of its termini and is capable of penetrating the cavity of CD. The size of the cavity can be estimated from that of the CD to be used on the basis of molecular modeling, molecular calculations, or the like; based on the estimated size, it is easy to estimate the kind and the length of a usable chain group. Furthermore, it is preferred that the parts other than both terminal groups for binding dye molecules or a chain group be chemically inert; such requirement also makes it easy to select the kind of chain group. Concrete chain groups which may be mentioned are methylene, polyether, polyamine, polyester and polyamide chains, etc.; or, the one that contains two or more of the foregoing. The use of a polymethylene chain is particularly preferable if it can be readily made adjustable in its length; it is chemically inert; and its molecular size is sufficiently small.

(2) The chain groups explained above are those which can bind dye molecules to both of their termini; and they may be such that they are capable of binding to the dye molecules in use, although their bonding methods are not particularly limited. As will be explained below, commercially available are a variety of dye molecules that can preferably be used in the invention and that are provided with various functional groups for binding to other substances. Alternatively, the dye molecules can be synthesized according to known methods. It is therefore easy to introduce into both termini of the chain group, groups capable of binding reaction with such functional groups. In this case, reactions that are ordinarily known in organic chemistry can be readily selected. Specifically, the combinations as shown below may preferably be selected.

| functional group of the dye molecule | binding group at the terminus of the chain group |
|---|---|
| isocyanate | amino, hydroxyl |
| carboxyl | amino, hydroxyl |
| acivated ester | amino, hydroxyl |
| amino | carboxyl |
| hydrazino | carboxyl |
| hydrazino | carbonyl |
| iodoacetoamide | thiol |
| maleimide | thiol |

In addition, the kinds of dye molecules binding to both termini of the chain group do not necessarily need to be the same. When different dye molecules are to be bound, it is easy to select some of the above-mentioned combinations based on their respective bonding methods.

Further, it is easy to select the length of the chain group based on the size of the cavity of CD. For example, in the case of a methylene chain, the chain is preferably longer than hexamethylene against α-, β-, or γ-CD. When the chain group is other than a methylene chain, it can be selected so that it will have a length greater than a hexamethylene chain—more preferably, greater than an octamethylene chain—per penetration through one CD ring if its length is converted to methylene chains. In the embodiment where penetration is through two or more CD rings, selection is readily made so that the length proves to be greater than that penetrating the respective CD rings.

3. Dye Molecules

The dye molecules for use in a rotaxane type dye according to this invention are to determine the presence of any substance to be detected by staining a specified substance with said rotaxane type dye or by labeling a specified substance to be detected and measuring the absorbance (or the reflected light) or the fluorescence of the labeled substance to be detected; they are not particularly limited. Depending on the embodiment how the present rotaxane type dye is used, it is possible to select dye molecules possessing a variety of properties. For example, they include various dye molecules for use in known dyestuff and pigments, as well as various dye molecules for use as tracers in vivo.

They further include dye molecules that are fluorescent. The rotaxane type dyes according to the invention contain CDs, which improve their water-solubility; therefore, it is not necessarily required that the dye molecules per se be water-soluble. Accordingly, not only water-soluble dye molecules known in the art but also dye molecules that are water-insoluble or sparingly water-soluble can preferably be used as long as they can be subject to the introduction of a suitable bonding group, as has been explained hereinabove.

Usable as a water-soluble fluorescent dye are, for example, a fluorescein type and a Rhodamine type. Concretely mentioned are carboxyfluorescein (FAM) and carboxytetramethyl Rhodamine (TAMRA). As a water-insoluble fluorescent dye, pyrene and the like are concretely mentioned.

In the case of a fluorescent dye molecule, selection of neither excitation wavelength nor fluorescence wavelength is limited. To increase fluorescence intensity, the same fluorescent dye molecules may be used. Where a plurality of different fluorescent molecules are used to take advantage of plural fluorescence, their combination is adequately selected with ease so that the excitation or fluorescence wavelengths of the respective fluorescent dye molecules may not overlap one another. Moreover, when a fluorescence energy transfer phenomenon between different fluorescent dyes is utilized, the relationship between a known energy-donor fluorescent dye molecule and a known energy-acceptor fluorescent dye molecule may be used. If the same energy-donor fluorescent dye molecules are combined with different energy-acceptor fluorescent dye molecules, a compound with multiple coloration in fluorescence wavelength caused by the same excitation wavelength is possible.

4. Synthetic Methods

Synthetic methods for a rotaxane type dye according to this invention are not particularly limited; and synthetic means in organic chemistry that are known in the art and that are used in the rotaxane synthesis can be employed. Generally, there is a method (i) by which CD, a dye molecule and a chain group are mixed together in a suitable solvent to form a rotaxane structure, and concurrently, bonding reaction between the dye molecule and the chain group is allowed to take place. According to this method, dimethylsulfoxide (DMSO), dimethylforamide (DMF) or the like, which is a nonpolar, nonaqueous solvent, is preferably usable as solvent. In addition, it is easy to optimize conditions such as reaction temperatures and times, depending on the kind of bonding reaction group.

There is also a method (ii) by which CD and a chain group are first mixed in a suitable solvent to obtain or isolate an inclusion compound and, thereafter, bonding reaction between the resulting inclusion compound and a dye molecule is allowed to take place. This method is especially favorable for the purpose of synthesizing the dye according to the invention having one kind of dye.

With respect to Synthetic Method (ii) described above, the particularly preferred method will be explained concretely in what follows. The conditions for the synthesis of a rotaxane from the chain group and the CD are most preferably such that the two phases, water and organic solvent, are employed to carry out the synthesis. Here, those which dissolve said chain group and which are sufficiently separable from water are usable as the organic solvent. For example, ethyl ether is mentioned. The chain group is dissolved (preferably saturated) in said organic solvent, or the CD is dissolved (preferably saturated) in water. The two phases are vigorously stirred at an appropriate temperature (preferably in the range of 30–50° C.). Such stirring causes the inclusion compound between the chain group and the CD to move into the water phase because it is dissolved chiefly in the water phase; this results in a mixture of the inclusion compound and the CD being present in the water phase. In this case, where the solubility of the obtained inclusion compound in water is less than that of the CD itself, a portion thereof may separate out from the water phase as a precipitate. Particularly, when said water phase is saturated with the CD, the precipitate often forms. Further, if desired, the precipitate can readily be obtained by cooling said water phase.

When the resulting precipitate does not substantially contain CD other than the inclusion compound, its isolation becomes feasible simply by filtration. In this case, if the resulting precipitate is further washed with ether, it will enable removal of the contaminating chain group.

When the CD is mingled with the inclusion compound in the resulting precipitate, an adequate separation means becomes necessary, for which a variety of chromatographic techniques is usable. Concretely, gel filtration (GPC), which is a method for separation based on molecular sizes, is preferably usable. Specifically, Sephadex G10 may be selected for the separation of α-CD from the inclusion compound between α-CD and don. Standard conditions are preferably usable for the GLC conditions. As for the monitoring of separation, TLC, HPLC, and the like are usable. It is preferred that water be used as an eluting solvent to minimize the equilibrium where the chain group is dislocated from the CD ring. Such separation means results in removal of the chain group which is contained in a small amount.

To allow dye molecules to react with and bind to the resulting inclusion compound, reactions that are ordinarily known in organic chemistry can be used. In this case, different dye molecules can be allowed to react and bind, and the selection of such conditions is easy.

Monitoring of reaction or identification and confirmation of reaction products is feasible by using ordinary analytical techniques in organic chemistry after separation and purification by ordinary separation means. Concretely usable are, among others, monitoring of the progress of reaction by TLC or HPLC; measurement such as infrared absorption spectroscopy, nuclear magnetic resonance spectroscopy, absorption spectroscopy, and fluorescence spectroscopy; and mass spectrometry.

For confirmation of the presence in solution, it is preferred that the retention times of peaks as obtained in HPLC under specified conditions be compared. Alternatively, the comparison of nuclear magnetic resonance spectra, absorption spectra, fluorescence spectra and the like is preferable.

For confirmation of the presence in solid state, it is preferred that the absorption peaks in a specified region of infrared absorption spectra (e.g., 2000–500 $cm^{-1}$) be compared. Alternatively, the comparison of molecular peaks by mass spectrometry (e.g., TOFMS) is preferable.

Figure 3:
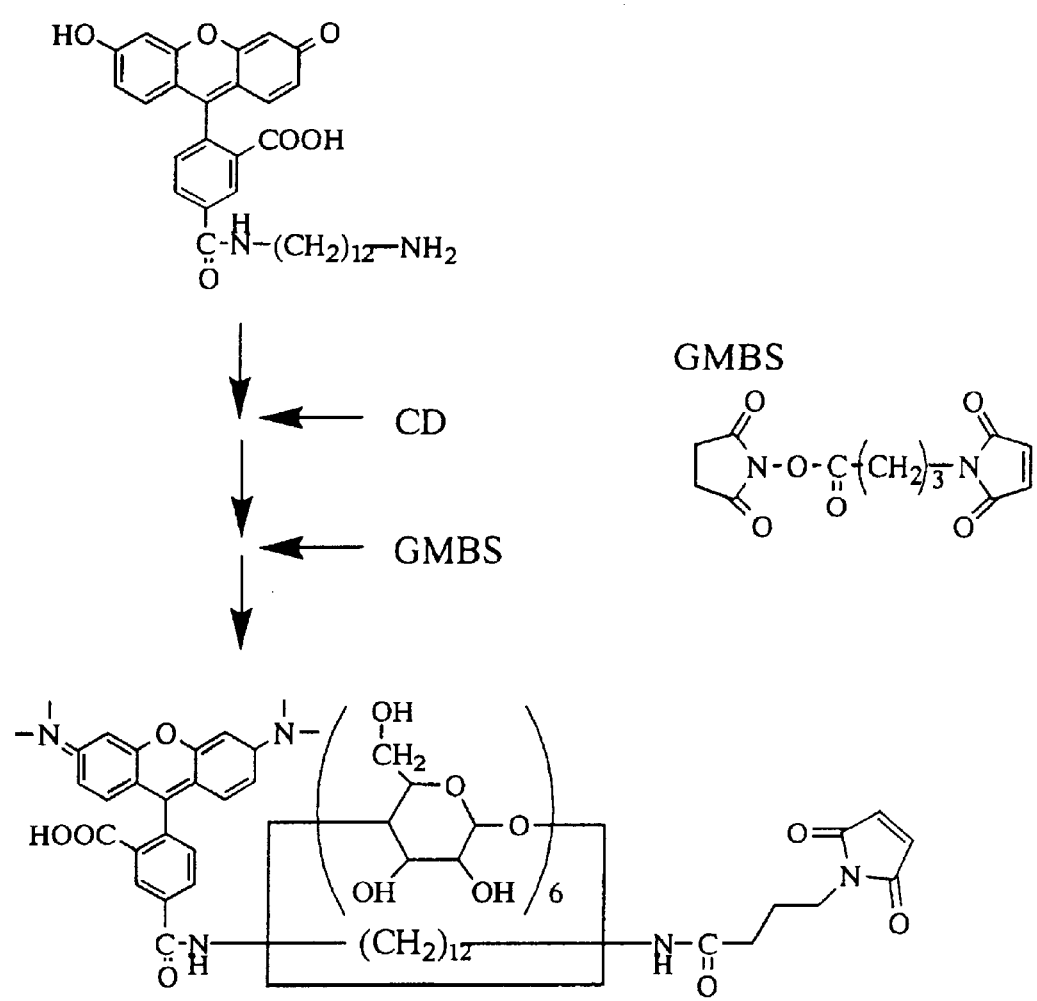
FIG. 3 is the representation of one example how one basic structure of the rotaxane type dye according to the invention is synthesized.

In FIG. 3 there is shown a synthetic method: after the chain group bound to a dye is allowed to react with CD to form an inclusion compound, the bonding group is allowed to react, which thus synthesizes another basic structure of the dye of this invention. The bonding group is readily selected based on chemically reactive groups that various substances to be labeled have. Specifically, a succinimidyl group or the like may be mentioned when the amino group of an amino acid, an oligopeptide, a protein, or the like is available for labeling. When a thiol group is available, a maleimide group, an alkylhalide group (which includes iodoacetoamide), etc may be mentioned. In addition, hydrazino and hydrazide groups may be mentioned for a carboxyl or carbonyl group; and an activated ester group and the like may be mentioned for a phenolic hydroxyl group.

Figure 4:
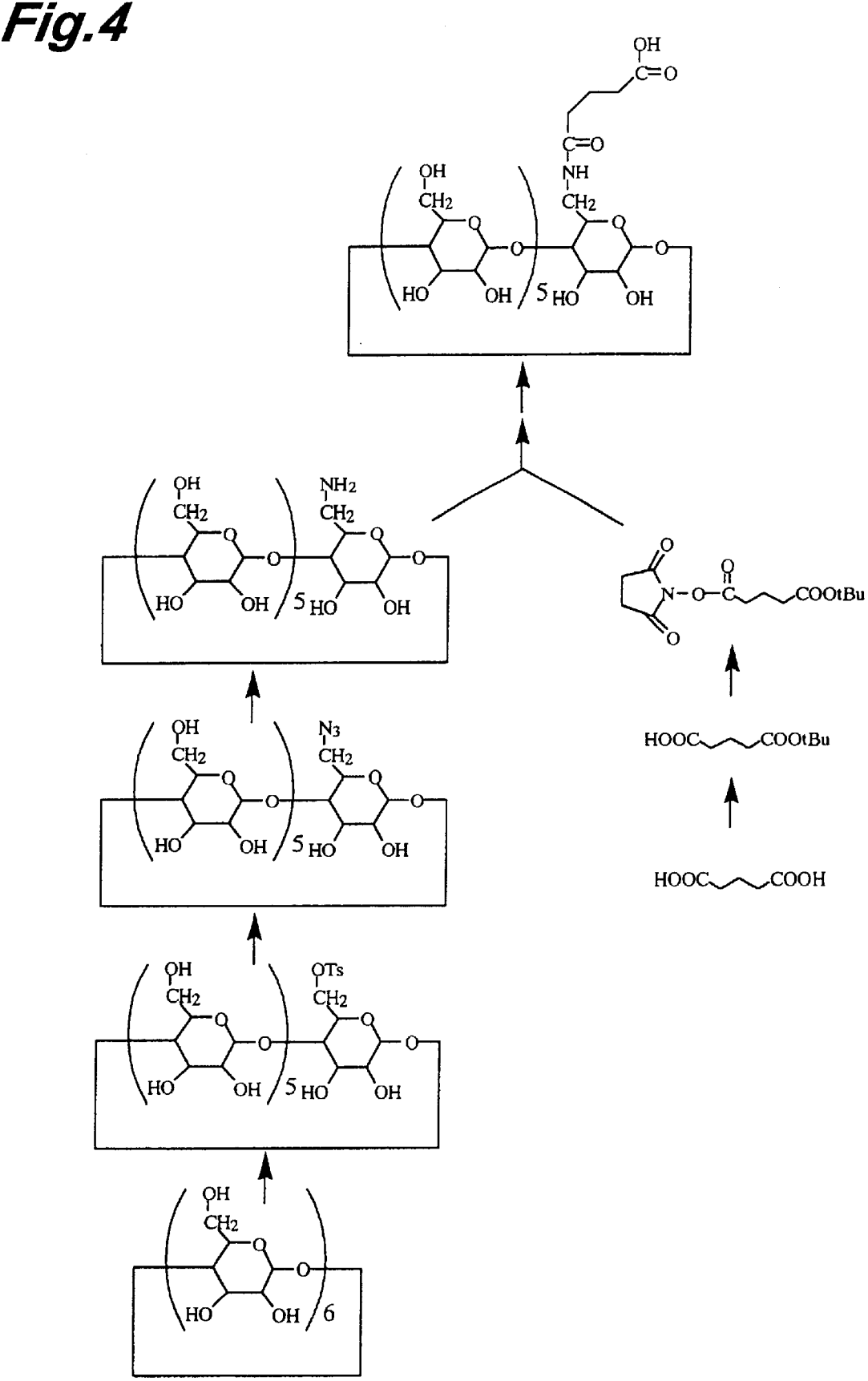
FIG. 4 is the representation of one example how a reactive group is introduced into one CD of a rotaxane type dye according to the invention.

Furthermore, FIG. 4 shows an example how a reactive group is introduced into CD: a reactive group having carboxyl at its terminus can be introduced, starting with hydroxyl and through amino.

5. Labeling Method

The rotaxane type dye according to this invention makes it possible to introduce a reactive group for labeling reaction into any of cyclodextrin, the dye molecule and the chain group. It becomes therefore possible to introduce various reactive groups for labeling reaction depending on the functional groups any compound to be labeled has. Concretely mentioned are a hydroxyl group of cyclodextrin, a halogenated compound (which is the derivative starting from the foregoing), amino, isocyanate, etc. Such reactive groups can be introduced according to ordinarily known methods. A variety of functional groups can also be introduced into a dye molecule. Concretely mentioned are carboxyl, amino, isocyanate, an activated ester group, etc. Such reactive groups can be introduced according to ordinarily known methods. A variety of functional groups can also be introduced into the chain group. Concretely mentioned are hydroxyl, a halogenated compound, carboxyl, amino, an activated ester group, isocyanate, etc. Such reactive groups can be introduced according to ordinarily known methods in organic synthesis.

The rotaxane type dyes according to this invention into which functional groups have been introduced (as explained above) become available for efficient labeling under mild conditions in aqueous solution. Although the selection of such reaction conditions may differ with respect to the labeling reaction, they can be readily optimized.

There are no particular limitations to substances to be labeled by the labeling methods relying on the rotaxane type dyes according to the invention; and numerous kinds of biological substances present in aqueous solution can be labeled. Preferably, the substance to be labeled has at least one functional group for reacting with a reagent according to the invention. However, where the substance to be labeled has no functional group for reacting with the reagent according to the invention, it is possible to introduce such functional group by suitable pretreatment. To this end, it is easy to utilize chemical reactions that are ordinarily known. Further, corresponding with said functional group of the substance to be labeled, the bonding group of a labeling agent according to the invention is readily selected as has been explained hereinabove. Concretely mentioned as the substance to be labeled are amino acid, sugar, peptide, nucleic acid, protein, etc. In such cases, the bonding reactions with the labeling agents according to the invention can be readily selected from techniques in organic chemistry that are ordinarily known. For example, in the case of an amino acid or a peptide, an amino group is available, and the bonding reaction becomes readily feasible by introducing an isocyanate or activated ester group into the dye molecule or cyclodextrin.

6. Detection Methods

When the rotaxane type dyes according to this invention are used as labeling agents, the methods for detecting said dyes are not particularly limited. The optimal method of detection can be selected depending on the dye molecules that have been used. For example, mentioned are a method based on the absorption of the dye molecules used, measurement of fluorescence spectra if they are of fluorescent nature, and the like. Especially, when the dye molecules used are fluorescent, methods of detection with high sensitivity that are known in the art or methods of specific detection are applicable, which will be explained in detail below.

(1) In the Case of a Rotaxane Type Dye According to the Invention Having One Kind of Fluorescent Dye Molecule Any substance labeled with the dye according to the invention emits fluorescence based on said fluorescent dye. Detection of this fluorescence has enabled the detection of the labeled substance. As has been explained hereinabove, the dye according to the invention is able to bind a plurality of one kind of fluorescent dye. In such case, the fluorescence intensity to be gained can be increased in proportion to the number of the fluorescent molecule, which makes it possible to improve detection sensitivity.

(2) In the Case of a Rotaxane Type Dye According to the Invention Having Two or More Kinds of Fluorescent Dye Molecule In this case, it is possible to detect the normal fluorescence spectrum of each fluorescent dye molecule as explained above; besides, detection methods based on various interactions between said fluorescent dye molecules are feasible. For example, the two kinds of fluorescent dye molecule are an energy-donor fluorescent dye and an energy-acceptor fluorescent dye; thus, there is mentioned a detection method that utilizes the fluorescence energy transfer phenomenon between those molecules. Furthermore, the two or more kinds of different fluorescent dye molecules are one energy-donor fluorescent dye and plural other energy-acceptor fluorescent dyes; thus, a detection method is possible that utilizes the fluorescence energy transfer phenomenon between those molecules. In this case, by exciting the single energy-donor fluorescent dye, it becomes possible to detect fluorescence emissions from the plural energy-acceptor fluorescent dyes.

7. Application Examples

If the rotaxane type dyes according to this invention are used, dye molecules that are intrinsically regarded as water-insoluble or sparingly water-soluble turn to be water-soluble due to the presence of cyclodextrin. This allows conventional dye molecules that are water-insoluble or sparingly water-soluble to be favorably usable in aqueous solution; it also eliminates the need to use nonaqueous solvents (organic solvents).

Concretely mentioned are those that allow the use of paint or dyestuff in aqueous solution either of which has been traditionally used in organic solvents. Also, mentioned is that the use of dyes for dye laser or for probe in aqueous solution is enabled. Furthermore, there is mentioned an application as various makers that are usable in vivo—aqueous solution—for the purpose of diagnosis, examination or medical treatment.

In addition, if any labeling agent containing plural rotaxane type dyes according to this invention is used, multicolor labeling becomes feasible. Namely, it is possible to individually label plural substances to be labeled (e.g., plural kinds of protein). For example, plural fluorescence labeling agents are used that have the same energy-donor fluorescent dyes (e.g., Dye 1 is made commonality in FIG. 1) and different energy-acceptor dyes (e.g., Dyes 2, 3, 4, etc in FIG. 1); by labeling plural corresponding substances—to be labeled—with them respectively, it is possible to monitor the respective substances to be labeled existing in a sample where such substances to be labeled are present as mingled. In this case, if the excitation light of Dye 1 (single excitation light) is irradiated, it becomes possible to separately measure fluorescence at the fluorescence wavelength of each energy-acceptor fluorescence dye (i.e., the fluorescence wavelength of Dye 2, 3, 4 or the like), according to the content of each substance to be labeled.

In view of the foregoing, an application is possible specifically in DNA sequencing dyes: Taking advantage of the characteristics that various wavelengths can be derived from one kind of excitation light, fluorescent dyes of four colors for use in DNA sequencing may be synthesized. The cells stained in multiplicity can also be detected efficiently. Whether the excitation is by a single wavelength or by multiple wavelengths, the range of combination of usable dyes may be extended by changing the donor dye or the acceptor dye. Additionally, clear images with low background can be expected because the Stokes shift increases. Another application as antibody-labeling dyes is possible in fluoroimmunoassay. Depending on the substances that are the subject of measurement, antibodies bound to dyes having different fluorescence wavelengths are prepared. This enables a group of substances in a sample such as blood, which are the subject of measurement, to be detected at one time. By making fluorescence measurement once at a single excitation wavelength with a photodiode or CCD, high sensitivity analysis can be carried out with an inexpensive device.

Figure 5A:
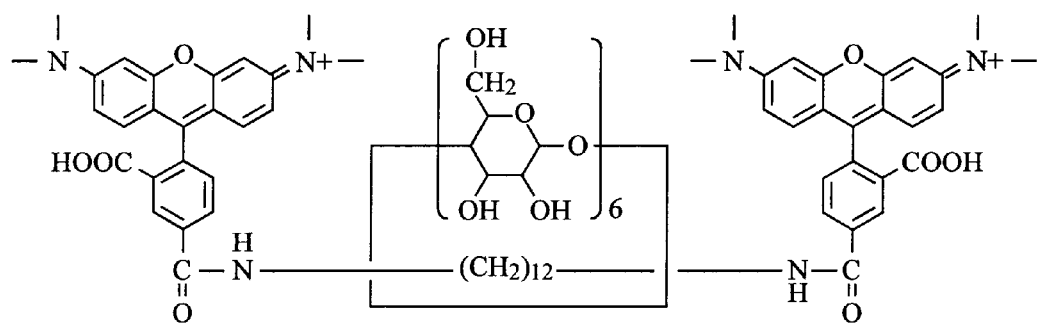
FIG. 5A is a representation of the structure of (TAMRA)-don-(TAMRA)-CD rotaxane as shown in the Examples of rotaxane type dyes according to the invention.
Figure 5B:
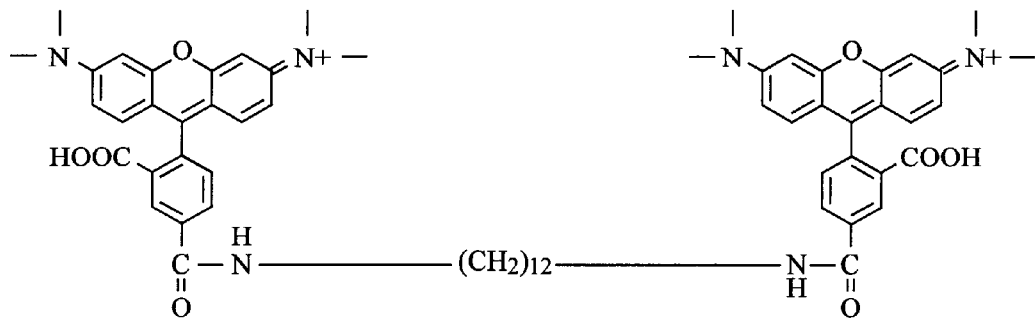
FIG. 5B is a representation of the structure of (TAMRA)-don-(TAMRA) as shown in the Examples of rotaxane type dyes according to the invention.
Figure 6A:
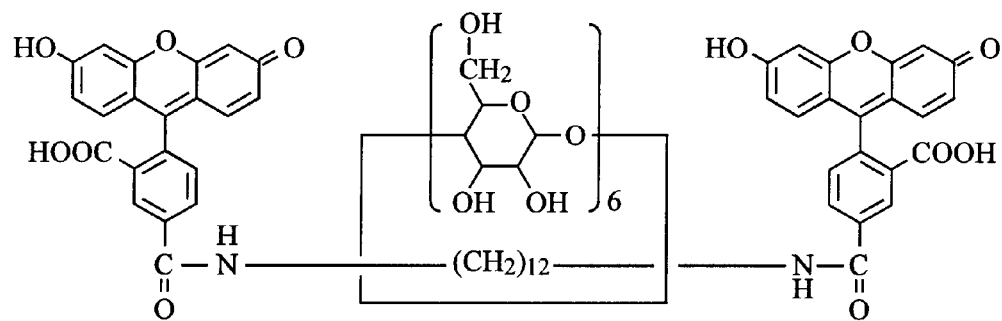
FIG. 6A is a representation of the structure of (FAM)-don-(FAM)-CD rotaxane, which is a rotaxane type dye according to the invention.
Figure 6B:
FIG. 6B is a representation of the structure of (FAM)-don-(FAM), which is a rotaxane type dye according to the invention.
Figure 7A:
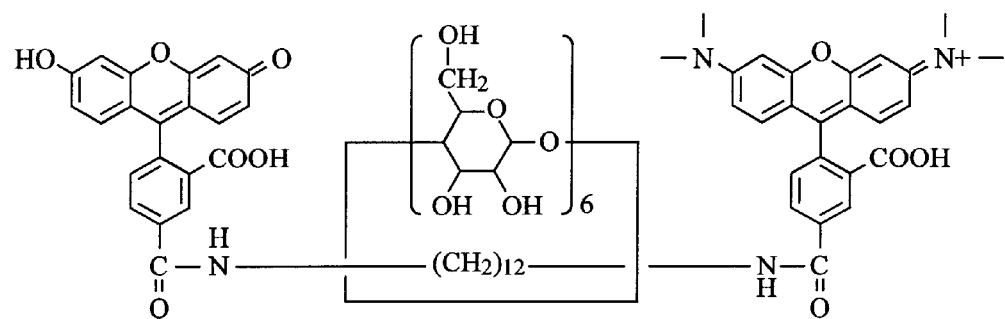
FIG. 7A is a representation of the structure of (FAM)-don-(TAMRA)-CD rotaxane as shown in the Examples of rotaxane type dyes according to the invention.
Figure 7B:
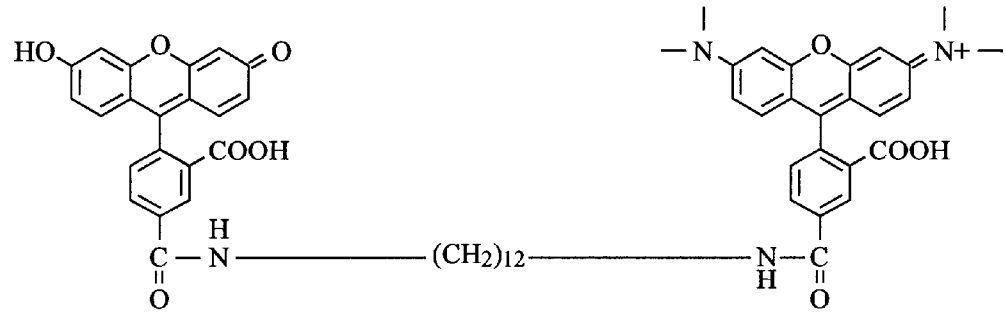
FIG. 7B is a representation of the structure of (FAM)-don-(TAMRA) as shown in the Examples of rotaxane type dyes according to the invention.

Here, "TAMRA" denotes "carboxytetramethyl Rhodamine," "FAM" denotes "carboxyfluorescein," and "don" denotes "diaminododecane" in the present specification. "(TAMRA)2-don-CD rotaxane" (or "(TAMRA)-don-(TAMRA)-CD rotaxane") denotes that its fluorescent dyes are both TAMRA, its chain group is don, and cyclodextrin furnishes it with a rotaxane structure (FIG. 5A). "(TAMRA)-don-(TAMRA)" denotes that its fluorescent dyes are both TAMRA and these are linked by the chain group don (FIG. 5B). "(FAM)2-don-CD rotaxane" (or "(FAM)-don-(FAM)-CD rotaxane") denotes that its fluorescent dyes are both FAM, its chain group is don, and cyclodextrin furnishes it with a rotaxane structure (FIG. 6A). "(FAM)-don-(FAM)" denotes that its fluorescent dyes are both FAM and these are linked by the chain group don (FIG. 6B). "(FAM)-don-(TAMRA)-CD rotaxane" denotes that its fluorescent dyes are TAMRA and FAM, its chain group is don, and cyclodextrin furnishes it with a rotaxane structure (FIG. 7A). "(FAM)-don-(TAMRA)" denotes that its fluorescent dyes are TAMRA and FAM and these are linked by the chain group don (FIG. 7B).

Figure 8A:
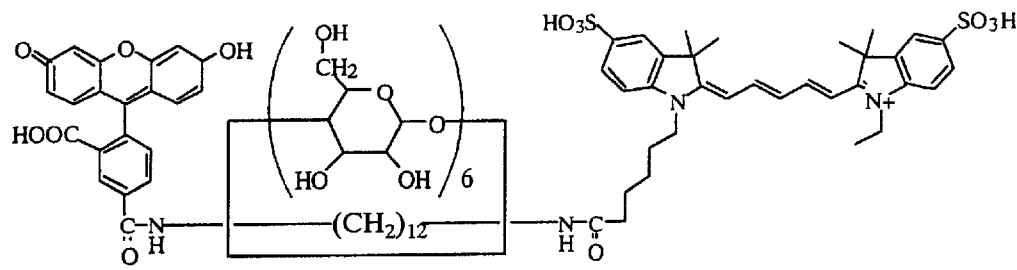
FIG. 8A is a representation of the structure of (FAM)-don-(Cy5)-CD rotaxane as shown in the Examples of rotaxane type dyes according to the invention.
Figure 8B:
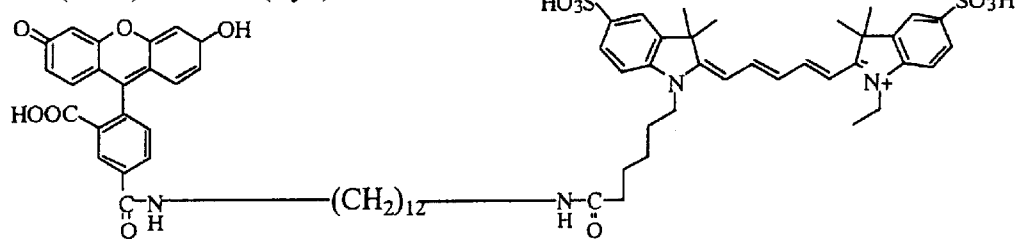
FIG. 8B is a representation of the structure of (FAM)-don-(Cy5) as shown in the Examples of rotaxane type dyes according to the invention.

"(FAM)-don-(Cy5)-CD rotaxane" denotes that its fluorescent dyes are FAM and Cy5, its chain group is don, and cyclodextrin furnishes it with a rotaxane structure (FIG. 8A). "(FAM)-don-(Cy5)" denotes that its fluorescent dyes are FAM and Cy5 and these are linked by the chain group don (FIG. 8B).

Figure 9:
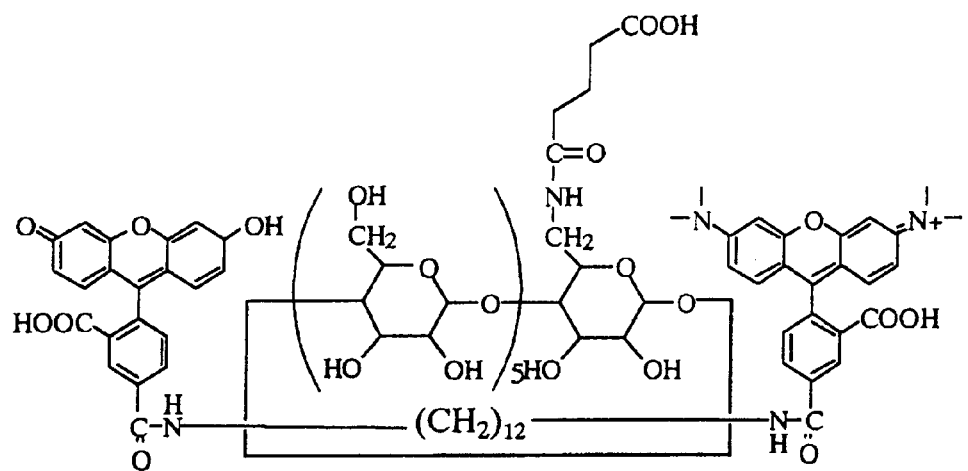
FIG. 9 is a representation of the structure of (FAM)-don-(TAMRA)-CDcooh rotaxane as shown in the Examples of rotaxane type dyes according to the invention.

"(FAM)-don-(TAMRA)-CDcooh rotaxane" denotes that it is provided with a structure having carboxyl formed by allowing the reactive group to react with the CD of the (FAM)-don-(TAMRA)-CD rotaxane fluorescent dye (FIG. 9).

More detailed explanation will be made hereinbelow by way of Examples.

EXAMPLE 1

Synthesis of (TAMRA)2-don-CD Rotaxane (I)

1,12-Diaminododecane (don) (3 mg, 15 µmol) was dissolved in 100 µl of a dimethyl sulfoxide (DMSO) solution saturated with α-cyclodextrin (hereinafter referred to as "α-CD") while stirring at 40° C. To this was added 5-carboxytetramethyl Rhodamine succinimidyl ester (5-TAMRA, SE) (25 mg, 47 µmol) dissolved in 50 µl of DMF and it was stirred at 40° C. overnight. The reaction solution was analyzed by high performance liquid chromatography (hereinafter referred to as "HPLC") under the conditions as described below, and it was ascertained that the retention time of 12.2 min was the desired substance. Fractionation and purification was done using preparative HPLC under the conditions as described below. After solvent was removed under reduced pressure from the fractions that had eluted (TAMRA)2-don-CD rotaxane, the desired component, the residual aqueous solution was dried by lyophilization to afford purple powders (8% yield).

Figure 10:
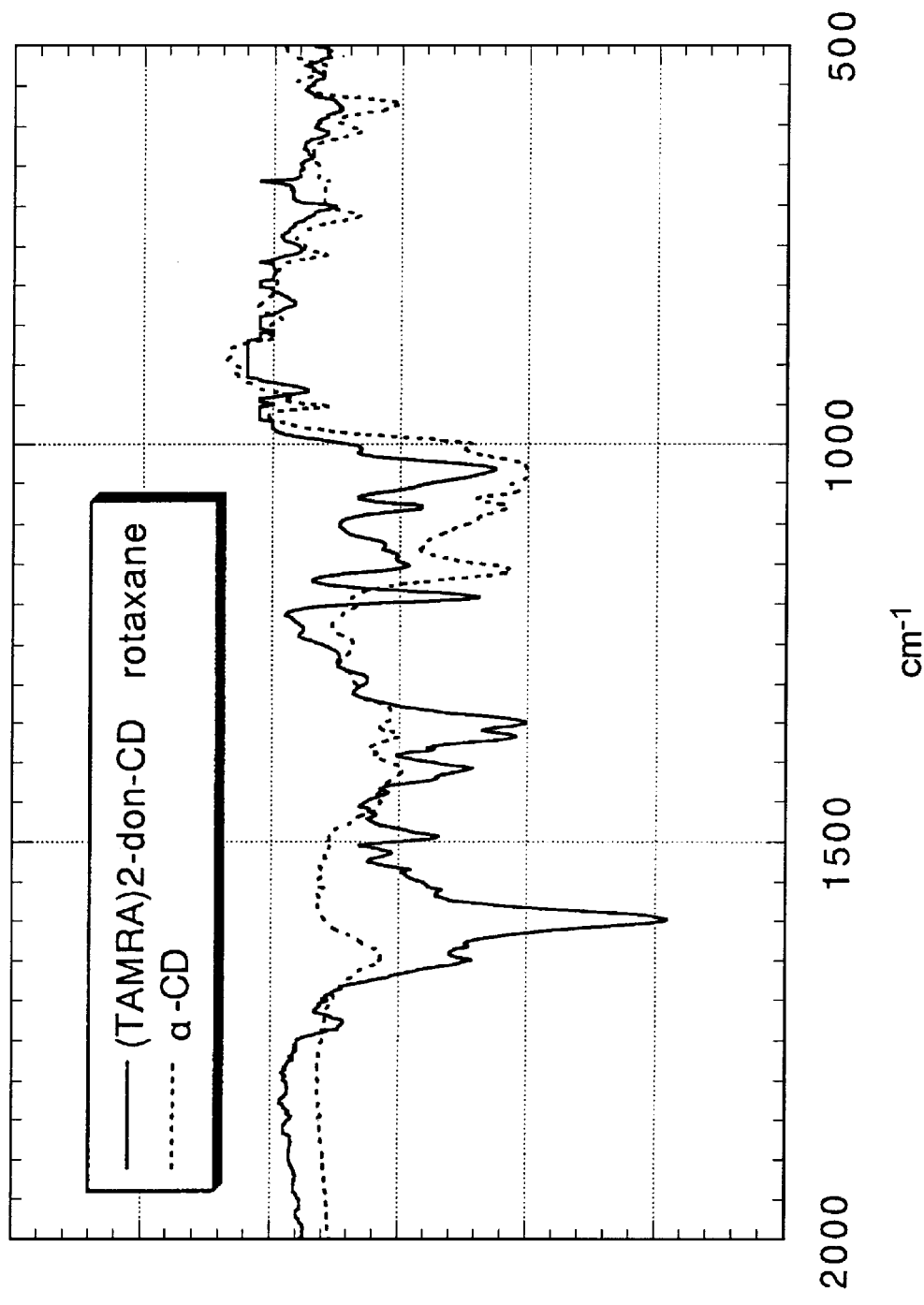
FIG. 10 is a graph showing the infrared absorption spectra of (TAMRA)-don-(TAMRA)-CD rotaxane and α-CD.
Figure 12:
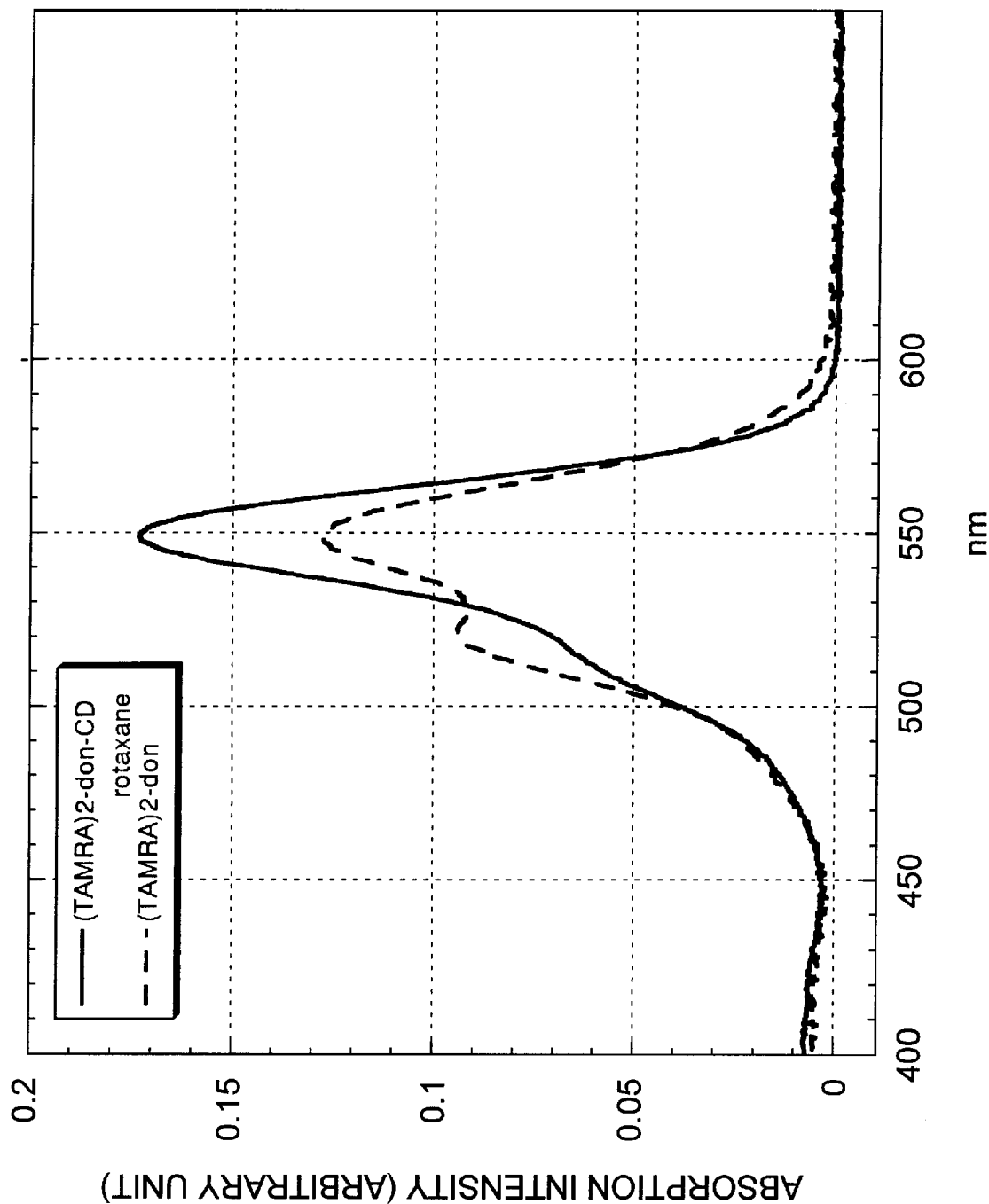
FIG. 12 is a graph showing the absorption spectra of (TAMRA)-don-(TAMRA)-CD rotaxane and (TAMRA)-don-(TAMRA) (at concentrations of $1.0\times10^{-6}$ M).

Analytical HPLC Apparatus and Analytical Conditions:
Device: Tosoh HPLC system
Detection: Hitachi ultraviolet and visible photometric detector L-7420 (546 nm); and Hitachi fluorescence detector L-7480 (excitation at 546 nm, emission at 590 nm)
Column: AsahipackODP-50 4E 4.6 mm×250 mm
Eluant: gradient of from 50% water (10 mM ammonium acetate)/50% methanol (10 mM ammonium acetate) to 100% methanol (10 mM ammonium acetate)
Flow rate: 0.6 ml/min
Mass Spectrometry:
Device: Shimadzu laser ionization time-flight type mass spectrometer (MALDI-IV)—the same device was used unless otherwise stated and will be hereinafter abbreviated as "TOF-MS."
Matrix: DHBA (gentisic acid)
[M+1]+: 2001
Absorption Spectrum (methanol): 543 nm (FIG. 12)
Fluorescence Spectrum (methanol): excitation at 543 nm and fluorescence emission at 578 nm
IR Spectrum (KBr): FIG. 10

EXAMPLE 2

Synthesis of (TAMRA)2-don-CD Rotaxane (II)
(Synthesis, Isolation and Identification of Inclusion Compound)

"don" was dissolved in diethyl ether at room temperature to prepare its saturated solution. Similarly, an aqueous saturated solution of α-CD was prepared. Each saturated solution, 0.5 ml, was placed in a sample tube, and under sealing, it was stirred at 40–50° C. overnight. After it was brought back to room temperature, only the aqueous phase was separated with a pipette. White precipitates formed in the resulting aqueous phase, and analytical results from their IR spectrum and the like ascertained that this white precipitation was the desired inclusion compound (a rotaxane between don and α-CD)

The aqueous phase after the reaction was washed with ether several times in a sample tube to remove don. Separation and purification of the inclusion compound was attempted using gel permeation chromatography (GPC), as will be explained below.

Specifically, the aqueous solution obtained above was applied to a Sephadex G10 GPC column, which will be described below, and the column was eluted with water. The initially eluted fractions contained the desired inclusion compound, but they also contained α-CD. The fractions that did not substantially contain free don were collected while being monitored with TLC (normal phase silica gel, chloroform/methanol 10:1) and the resulting fractions were concentrated.

(Synthesis of (TAMRA)2-don-CD Rotaxane)
To the aqueous solution of the inclusion compound as obtained above was added 5-carboxytetramethyl Rhodamine succinimidyl ester (5-TAMRA, SE) (5 mg, 1 ml of DMF solution) and it was stirred at room temperature overnight. Column chromatography of the resulting reaction solution by means of Chromatorex NH-DM 3050 separated three kinds of compound—(TAMRA)2-don-CD rotaxane, (TAMRA)-don-CD, and α-CD. The fractionated components were concentrated under reduced pressure to remove acetonitrile and the residue was lyophilized (30% yield).
Conditions for Separation of the Inclusion Compound From Non-inclusion CD:
Column: Sephadex G10 10 mm×70 mm
Monitoring: The inclusion compound appeared in the vicinity of the starting point on TLC (silica gel, developing solvent: chloroform/methanol 10:1).

Conditions for Separation of (TAMRA)2-don-CD Rotaxane:
  Column: Chromatorex NH-DM3050 20 mm×250 mm (available from Fuji Sicilia Chemicals Co. Ltd.)
  Eluant: 70% acetonitrile
  Monitoring: TLC (HPTLC-NH-F-254 available from Merk AG., developing solvent: 70% acetonitrile)

EXAMPLE 3

Synthesis of (TAMRA)-don-(TAMRA)

1,12-Diaminododecane (don) (3 mg, 15 μmol) was dissolved in 100 μl of methanol, while stirring at 40° C. To this was added 5-carboxytetramethyl Rhodamine succinimidyl ester (5-TAMRA, SE) (25 mg, 47 μmol) dissolved in 50 μl of DMF and it was stirred at 40° C. overnight. The reaction solution was fractionated by HPLC and purified. After solvent was removed under reduced pressure from the fractions that had eluted (TAMRA)-don-(TAMRA), the desired component, the residual aqueous solution was lyophilized to afford purple powders.

Figure 11:
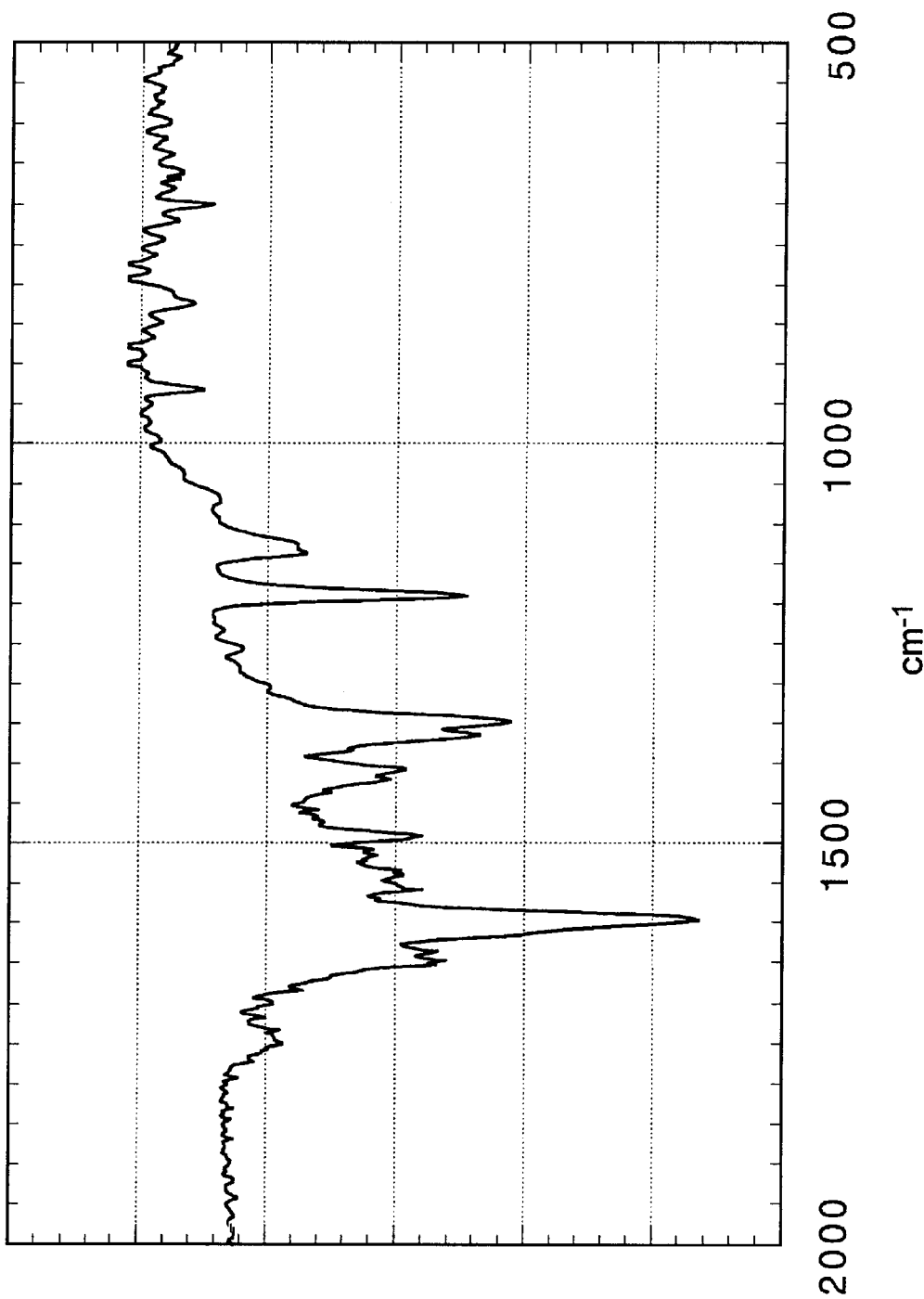
FIG. 11 is a graph showing the infrared absorption spectrum of (TAMRA)-don-(TAMRA).

Analytical HPLC Apparatus and Analytical Conditions:
  Device: Tosoh HPLC system
  Detection: Hitachi ultraviolet and visible photometric detector L-7420 (546 nm); and Hitachi fluorescence detector L-7480 (excitation at 546 nm, emission at 590 nm)
  Column: AsahipackODP-50 4E 4.6 mm×250 mm
  Eluant: gradient of from water 50% (10 mM ammonium acetate)/50% methanol (10 mM ammonium acetate) to 100% methanol (10 mM ammonium acetate)
  Flow rate: 0.6 ml/min
Mass Spectrometry:
  Device: Shimadzu laser ionization time-flight type mass spectrometer (MALDI-IV)
  Matrix: DHBA (gentisic acid)
  [M+1]+: 1028
Absorption Spectrum (methanol): 543 nm (FIG. 12)
Fluorescence Spectrum (methanol): excitation at 543 nm and fluorescence emission at 578 nm
IR Spectrum (KBr): FIG. 11

EXAMPLE 4

Synthesis of FAM-don 1,12-Diaminododecane (don) (84.5 mg, 420 μmol) was completely dissolved in 1.8 ml of methanol. To this was added 5-carboxyfluorescein succinimidyl ester (5-FAM, SE) (10 mg, 20 μmol) dissolved in 400 μl of DMF dropwise in small amounts. After the dropwise addition was over, it was stirred at 40° C. overnight. The reaction solution was analyzed by HPLC, which ascertained that the 18.0 min was the desired substance. Then, fractionation and purification was done using preparative HPLC. After solvent was removed under reduced pressure from the fractions that had eluted (FAM)-don, the desired component, the residual aqueous solution was lyophilized to afford orange powders (7.6 mg).

Figure 13:
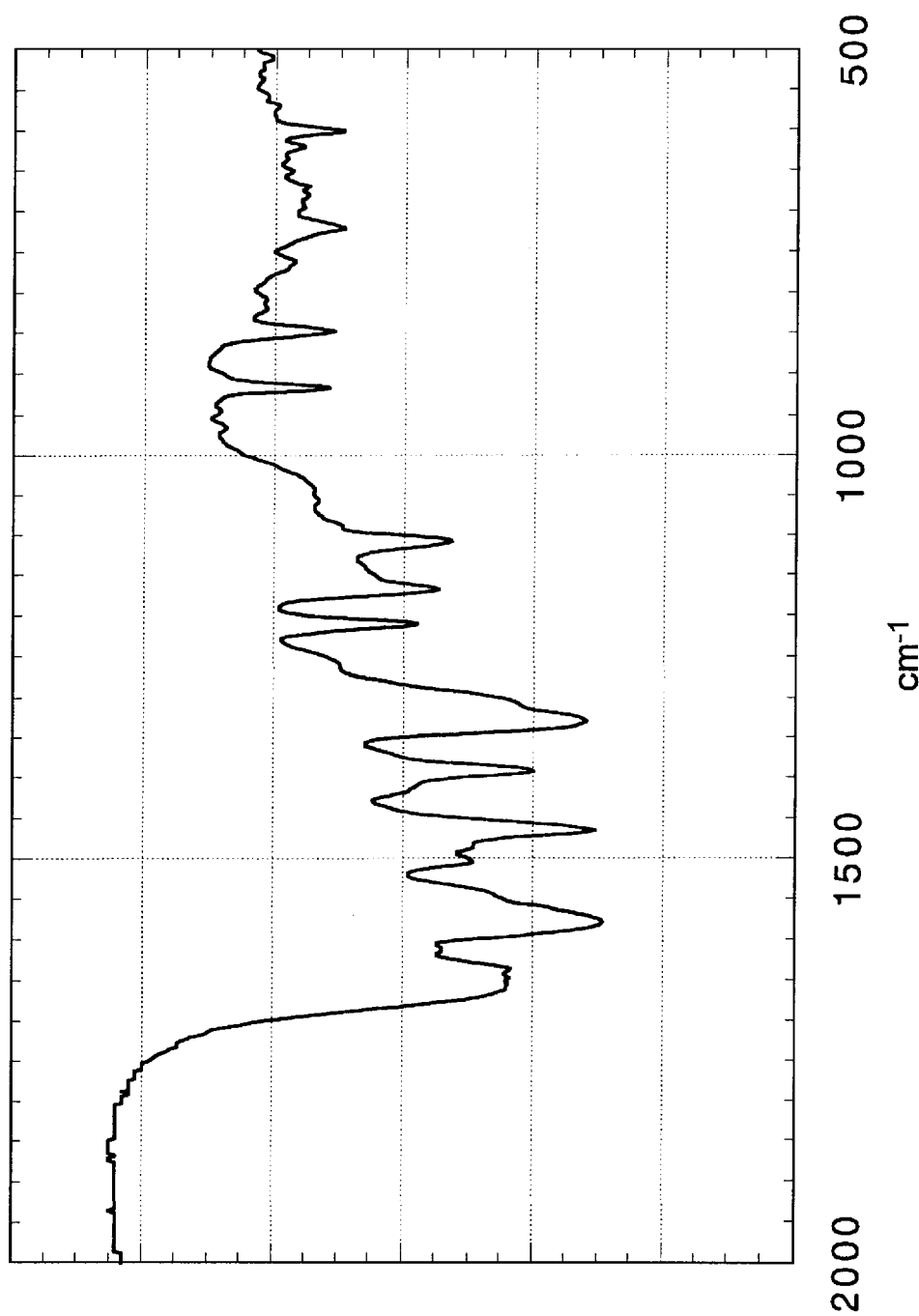
FIG. 13 is a graph showing the infrared absorption spectrum of (FAM)-don.
Figure 17:
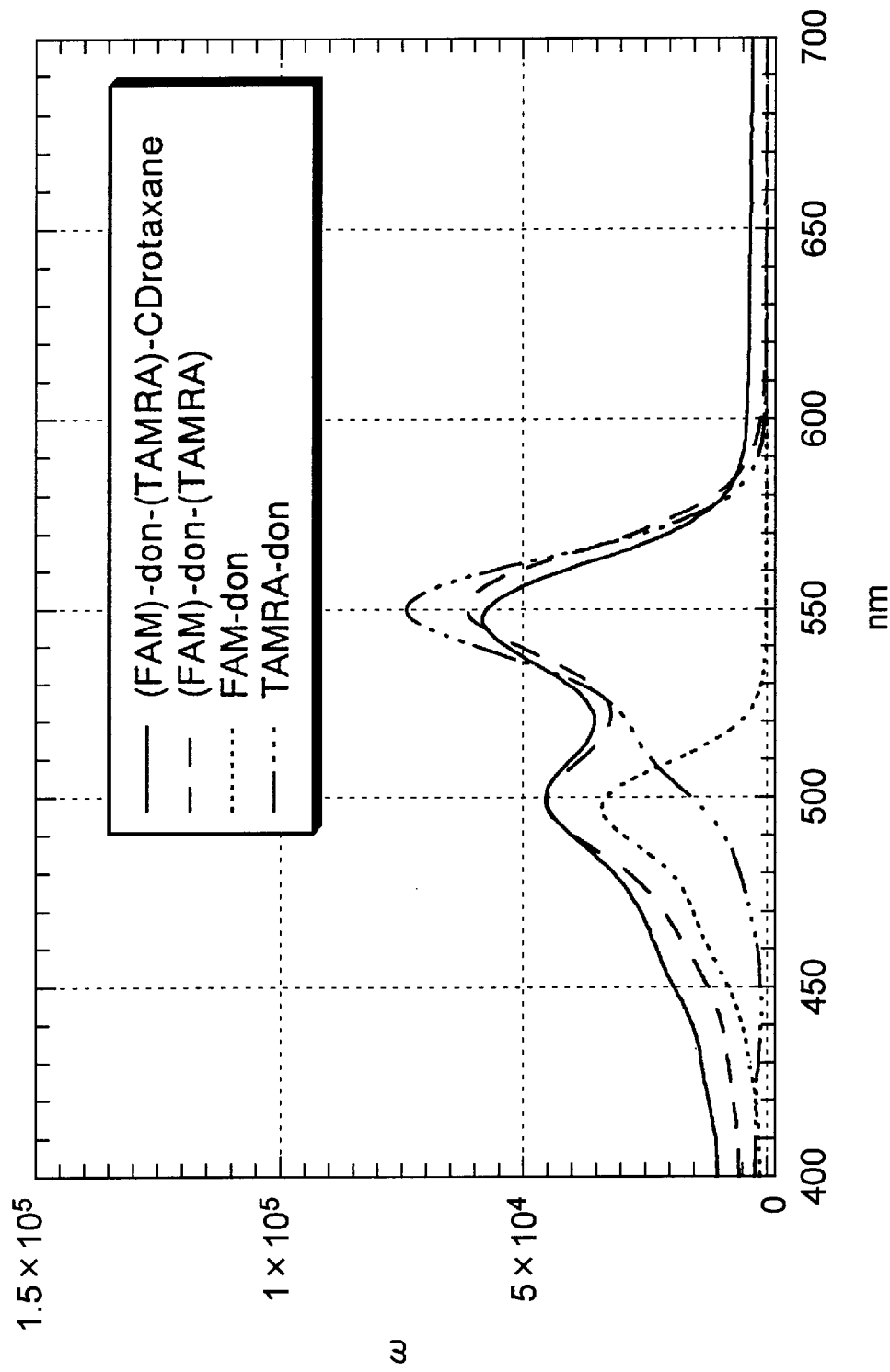
FIG. 17 is a graph showing the absorption spectra of (FAM)-don-(TAMRA)-CD rotaxane, (FAM)-don, and (TAMRA)-don in methanol/water (1:1).

Analytical HPLC Apparatus and Analytical Conditions:
  Device: Tosoh HPLC system
  Detection: Hitachi ultraviolet and visible photometric detector L-7420 (495 nm); and Hitachi fluorescence detector L-7480 (excitation at 495 nm, emission at 520 nm)
  Column: AsahipackODP-50 4E 4.6 mm×250 mm
  Eluant: gradient of from 50% water (10 mM ammonium acetate)/50% methanol (10 mM ammonium acetate) to 100% methanol (10 mM ammonium acetate)
  Flow rate: 0.6 ml/min
  Retention time: FAM-don at 18.5 min Preparative HPLC Apparatus and Preparative Conditions:
  Device: available from Tosoh Co. Ltd.
  Detection: ultraviolet and visible photometric detector UV-8020 (495 nm)
  Column: AsahipackODP-90 21F 21.4 mm×300 mm
  Eluant: gradient of from 45% water (10 mM ammonium acetate)/55% methanol (10 mM ammonium acetate) to 5% water (10 mM ammonium acetate)/95% methanol (10 mM ammonium acetate)
  Flow rate: 5 ml/min
Mass Spectrometry:
  Matrix: DHBA (gentisic acid)
  [M+1]+: 559
Absorption Spectrum (methanol): 499 nm (FIG. 17)
Fluorescence Spectrum (methanol): excitation at 499 nm and fluorescence emission at 525 nm
IR Spectrum (KBr): FIG. 13

EXAMPLE 5

Synthesis of (FAM)-don-(TAMRA)-CD Rotaxane

Figure 16:
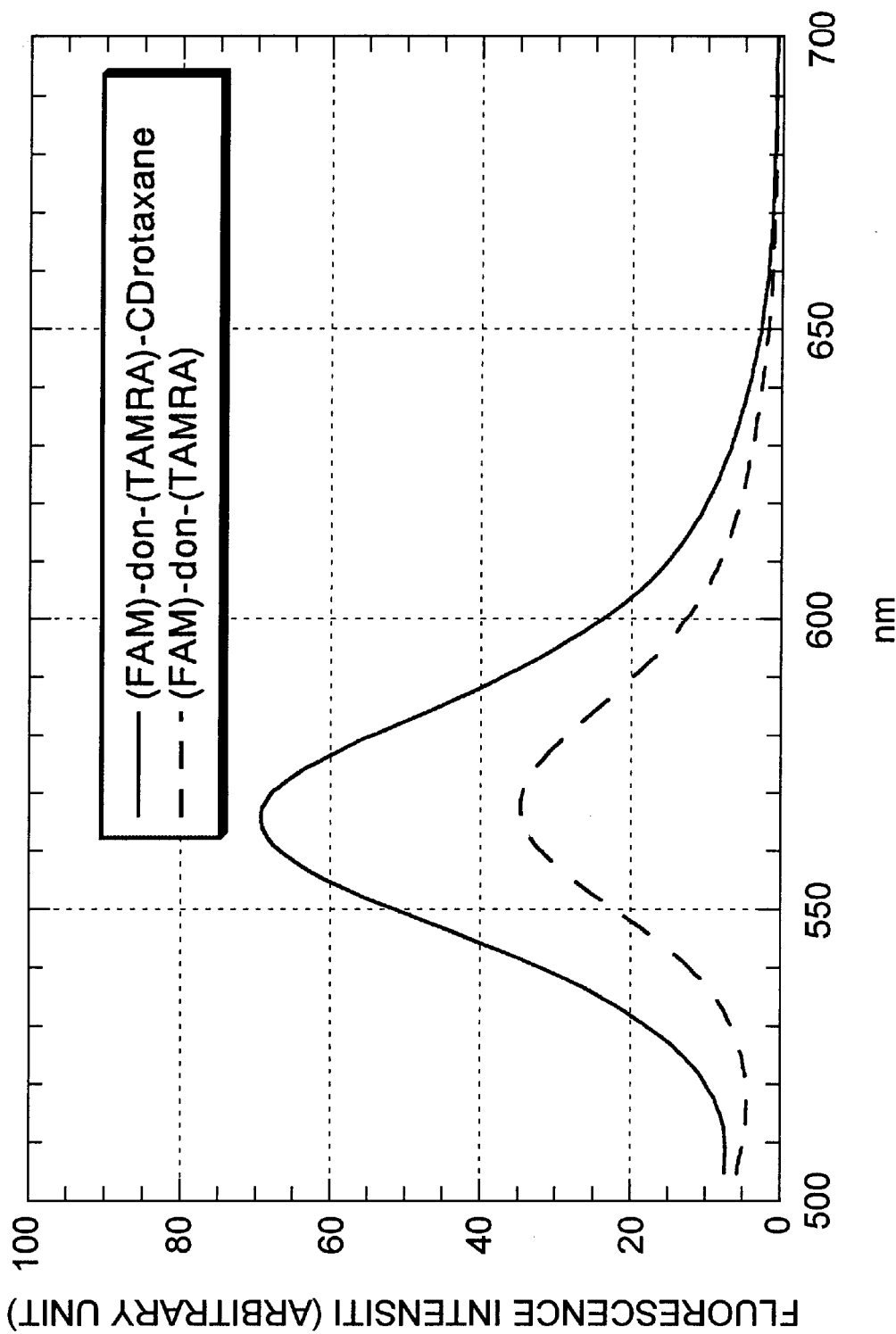
FIG. 16 is a graph showing the fluorescence spectra of (FAM)-don-(TAMRA)-CD rotaxane and α-CD at 499 nm emission (at concentrations of $1.0\times10^{-7}$ M).

The obtained (FAM)-don (7.6 mg, 13.6 μmol) was dissolved in 1.4 ml of a DMSO solution saturated with α-cyclodextrin (α-CD) and upon stirring at 40° C. for 2 days, it was allowed to be included by the CD. To this was added 5-carboxytetramethyl Rhodamine succinimidyl ester (5-TAMRA, SE) (10 mg, 18.9 μmol) dissolved in 400 μl of DMF and it was stirred for an additional day. The reaction solution was analyzed by HPLC, which could ascertained that the 6.4 min was the desired substance and the unreacted TAMRA. Then, fractionation and purification was done using preparative HPLC. The fractions that had eluted (FAM)-don-(TAMRA)-CD rotaxane, the desired substance, were concentrated and the desired substance was separated from the unreacted TAMRA by HPLC using a gel filtration column. After having ascertained that the retention time of 9.0 min was the desired substance, fractionation and purification was done using preparative HPLC. Solvent was removed under reduced pressure from the eluted fractions, the residual aqueous solution was lyophilized to afford purple powders. In the fluorescence spectrum of the resulting substance (FIG. 16), the fluorescence of the acceptor dye (Rhodamine) was confirmed when excitation was carried out at the absorption maximum wavelength (499 nm) of the donor dye (fluorescein). This indicates that the intramolecular fluorescence energy transfer has occurred.

Figure 14:
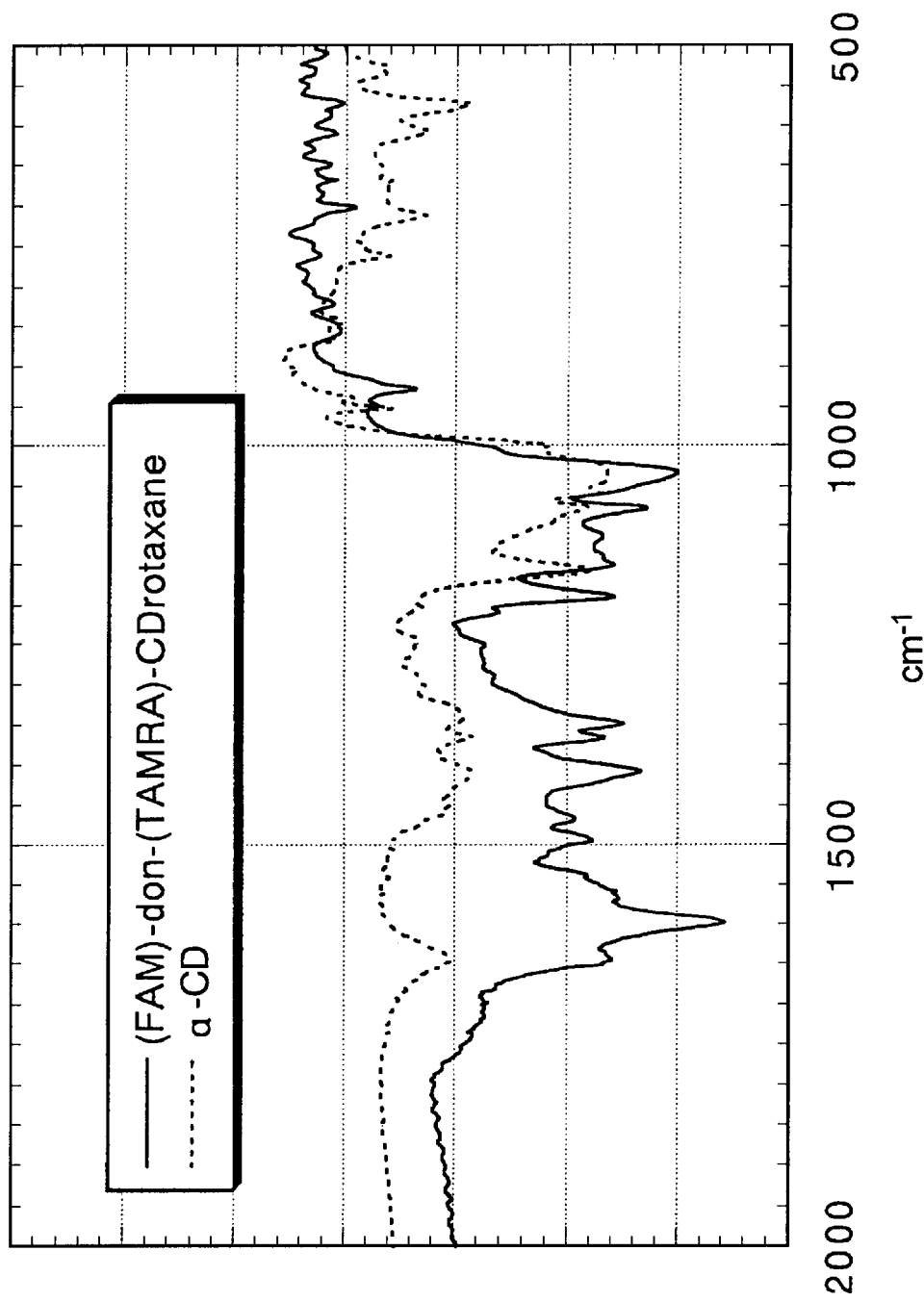
FIG. 14 is a graph showing the infrared absorption spectra of (FAM)-don-(TAMRA)-CD rotaxane and α-CD.

Analytical HPLC Apparatus and Analytical Conditions:
  Device: Tosoh HPLC system
  Detection: Hitachi ultraviolet and visible photometric detector L-7420 (495 nm); and Hitachi fluorescence detector L-7480 (excitation at 495 nm, emission at 580 nm)
  Column: AsahipackODP-50 4E 4.6 mm×250 mm
  Eluant: gradient of from 50% water (10 mM ammonium acetate)/50% methanol (10 mM ammonium acetate) to 100% methanol (10 mM ammonium acetate)
  Flow rate: 0.6 ml/min
  Retention time: (FAM)-don-(TAMRA)-CD rotaxane and TAMRA both at 6.4 min
  Device: Tosoh HPLC system
  Detection: Hitachi ultraviolet and visible photometric detector L-7420 (495 nm); and Hitachi fluorescence detector L-7480 (excitation at 495 nm, emission at 580 nm)
  Column: YMC-pack Diol-60
  Eluant: 50% water (10 mM ammonium acetate)/50% methanol (10 mM ammonium acetate)
  Flow rate: 1.0 ml/min
  Retention time: (FAM)-don-(TAMRA)-CD rotaxane at 9.0 min Preparative HPLC Apparatus and Preparative Conditions:
  Device: Tosoh HPLC system
  Detection: ultraviolet and visible photometric detector UV-8020 (546 nm)
  Column: AsahipackODP-90 21F 21.4 mm×300 mm
  Eluant: gradient of from 45% water (10 mM ammonium acetate)/55% methanol (10 mM ammonium acetate) to 5% water (10 mM ammonium acetate)/95% methanol (10 mM ammonium acetate)
  Flow rate: 5 ml/min
  Device: Tosoh HPLC system
  Detection: ultraviolet and visible photometric detector UV-8020 (546 nm)
  Column: YMC-Pack Diol-60
  Eluant: 50% water (10 mM ammonium acetate)/50% methanol (10 mM ammonium acetate)
  Flow rate: 6 ml/min
Mass Spectrometry:
  Matrix: DHBA (gentisic acid)
  [M+1]+: 1943
Absorption Spectrum (methanol): 499 nm, 548 nm (FIG. 17)
Fluorescence Spectrum (methanol): excitation at 499 nm and fluorescence emission at 573 nm (FIG. 16)
IR Spectrum (KBr): FIG. 14

EXAMPLE 6

Synthesis of (FAM)-don-(TAMRA)

Figure 15:
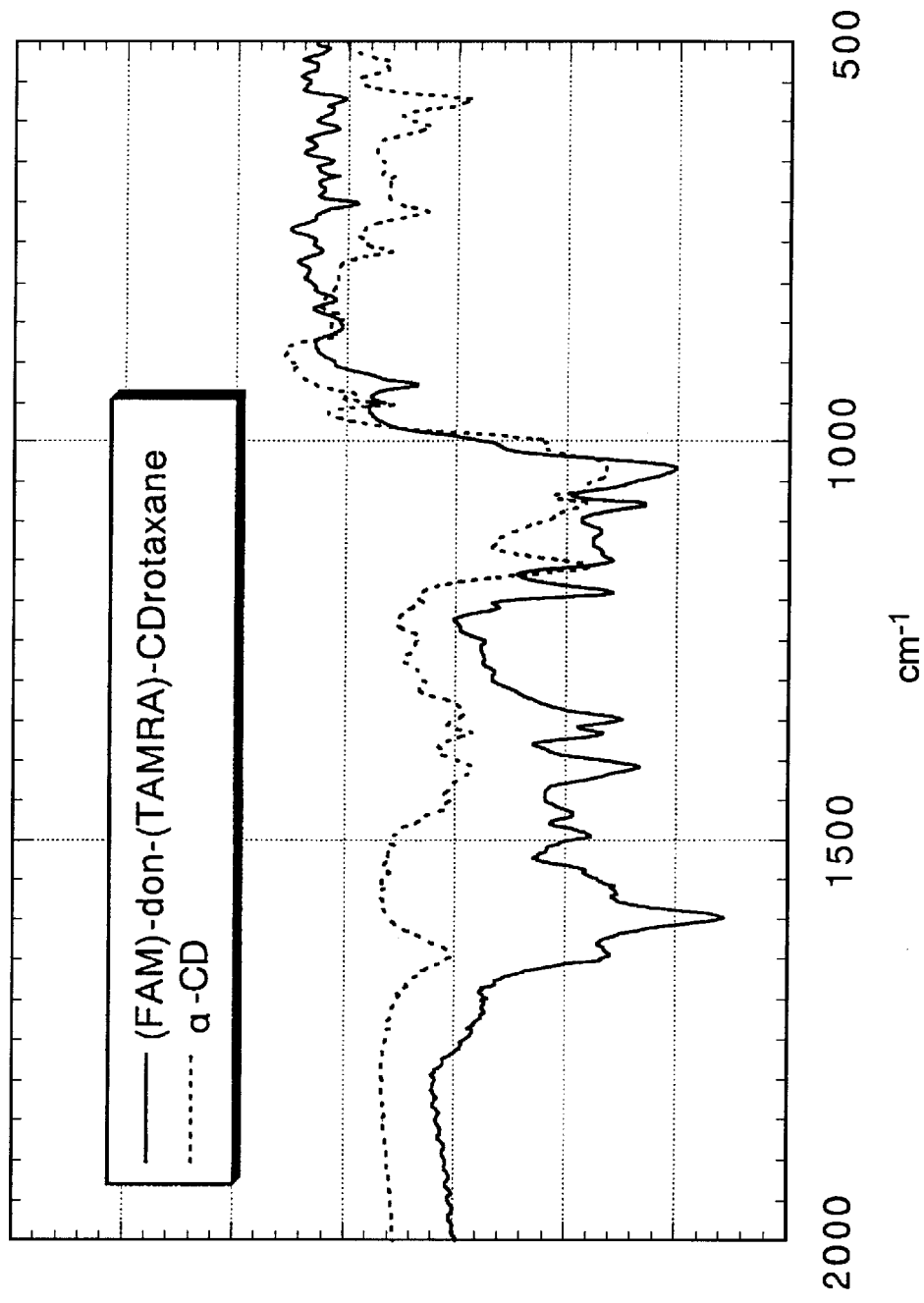
FIG. 15 is a graph showing the infrared absorption spectrum of (FAM)-don-(TAMRA).

The obtained (FAM)-don (7.6 mg, 13.6 μmol) was dissolved in 400 μl of methanol. To this was added 5-carboxytetramethyl Rhodamine succimidyl ester (5-TAMRA, SE) (10 mg, 18.9 μmol) dissolved in 400 μl of DMF and it was stirred at 40° C. for 1 day. The reaction solution was analyzed by HPLC, which ascertained that the 24.5 min was the desired substance. Then, fractionation and purification was done using preparative HPLC. Solvent was removed under reduced pressure from the fractions that had eluted (FAM)-don-(TAMRA), the desired substance, and the residual aqueous solution was lyophilized to afford purple powders.
Analytical HPLC Apparatus and Analytical Conditions:
  Device: Tosoh HPLC system
  Detection: Hitachi ultraviolet and visible photometric detector L-7420 (495 nm); and Hitachi fluorescence detector L-7480 (excitation at 495 nm, emission at 580 nm)
  Column: AsahipackODP-50 4E 4.6 mm×250 mm
  Eluant: gradient of from 50% water (10 mM ammonium acetate)/50% methanol (10 mM ammonium acetate) to 100% methanol (10 mM ammonium acetate)
  Flow rate: 0.6 ml/min
  Retention time: (FAM)-don-(TAMRA) at 24.5 min
Mass Spectrometry:
  Matrix: DHBA (gentisic acid)
  [M+1]+: 970
Absorption Spectrum (methanol): 500 nm and 542 nm (FIG. 17)
Emission Spectrum (methanol): excitation at 500 nm and emission at 569 nm (FIG. 16)
IR Spectrum (KBr): FIG. 15

EXAMPLE 7

Labeling Reaction of Phenetylamine (TAMRA)2-don-CD rotaxane (100 pmol) was dissolved in 20 μl of methanol. To this was added 25 μl of a 1M phenetylamine methanol solution and it was stirred together with 1-ethyl-3-(3-dimethylaminopropyl)-carbodiimide (EDC), 50 μg, and dimethylaminopyridine, 500 μg, at 40° C. for 1 day. The reaction solution was analyzed by HPLC, which ascertained that the 21.5 min was phenetylamine labeled with the rotaxane dye.
Analytical HPLC Apparatus and Analytical Conditions:
  Device: Tosoh HPLC system
  Detection: Hitachi ultraviolet and visible photometric detector L-7420 (546 nm); and Hitachi fluorescence detector L-7480 (excitation at 546 nm, emission at 600 nm)
  Column: AsahipackODP-50 4E 4.6 mm×250 mm
  Eluant: gradient of from 50% water (10 mM ammonium acetate)/50% methanol (10 mM ammonium acetate) to 100% methanol (10 mM ammonium acetate)
  Flow rate: 0.6 ml/min
Mass Spectrometry:
  Matrix: DHBA (gentisic acid)
  [M+1]+: 2205

EXAMPLE 8

Figure 18:
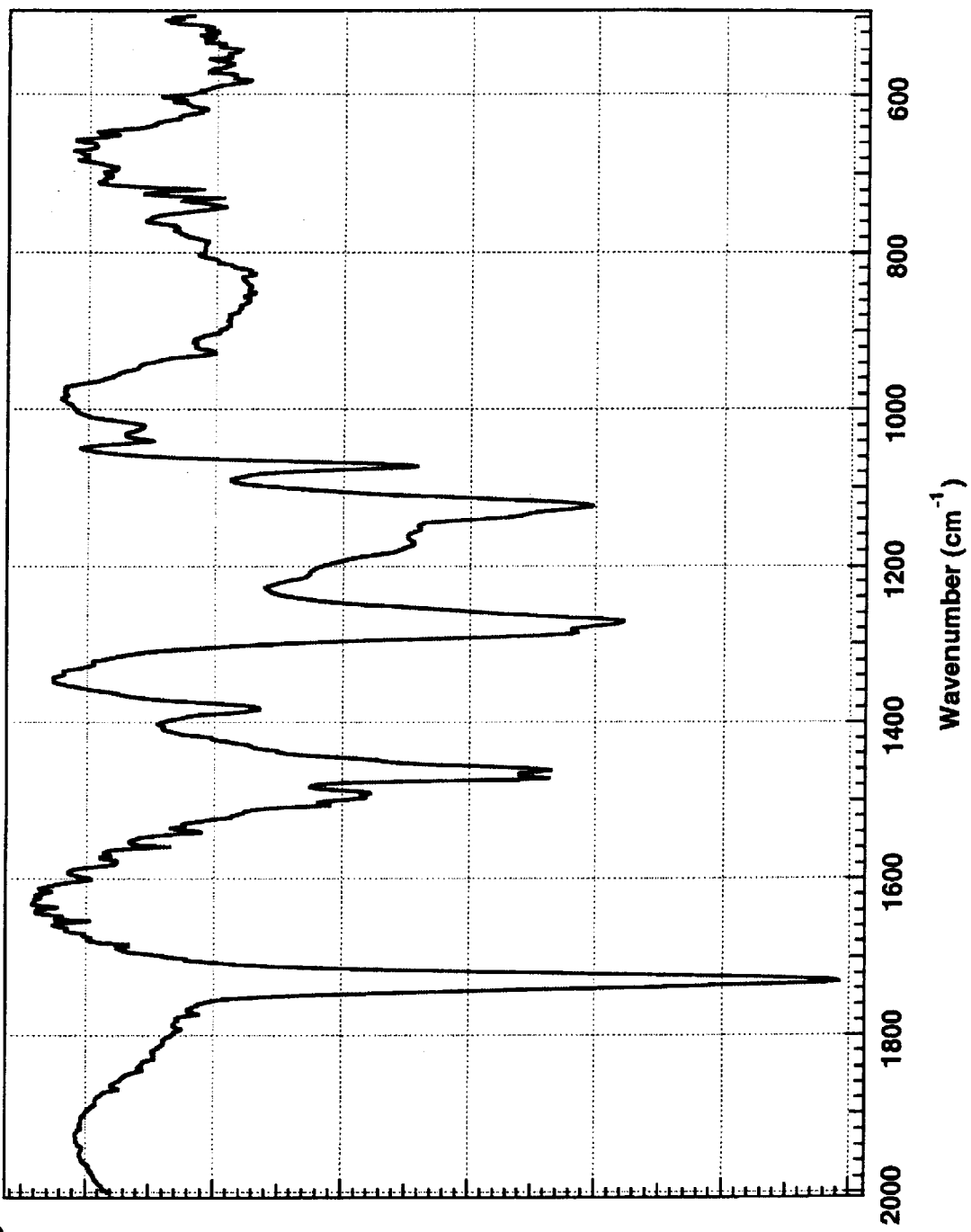
FIG. 18 is a graph showing the infrared absorption spectrum of (FAM)-don-(Cy5)-CD rotaxane.
Figure 20:
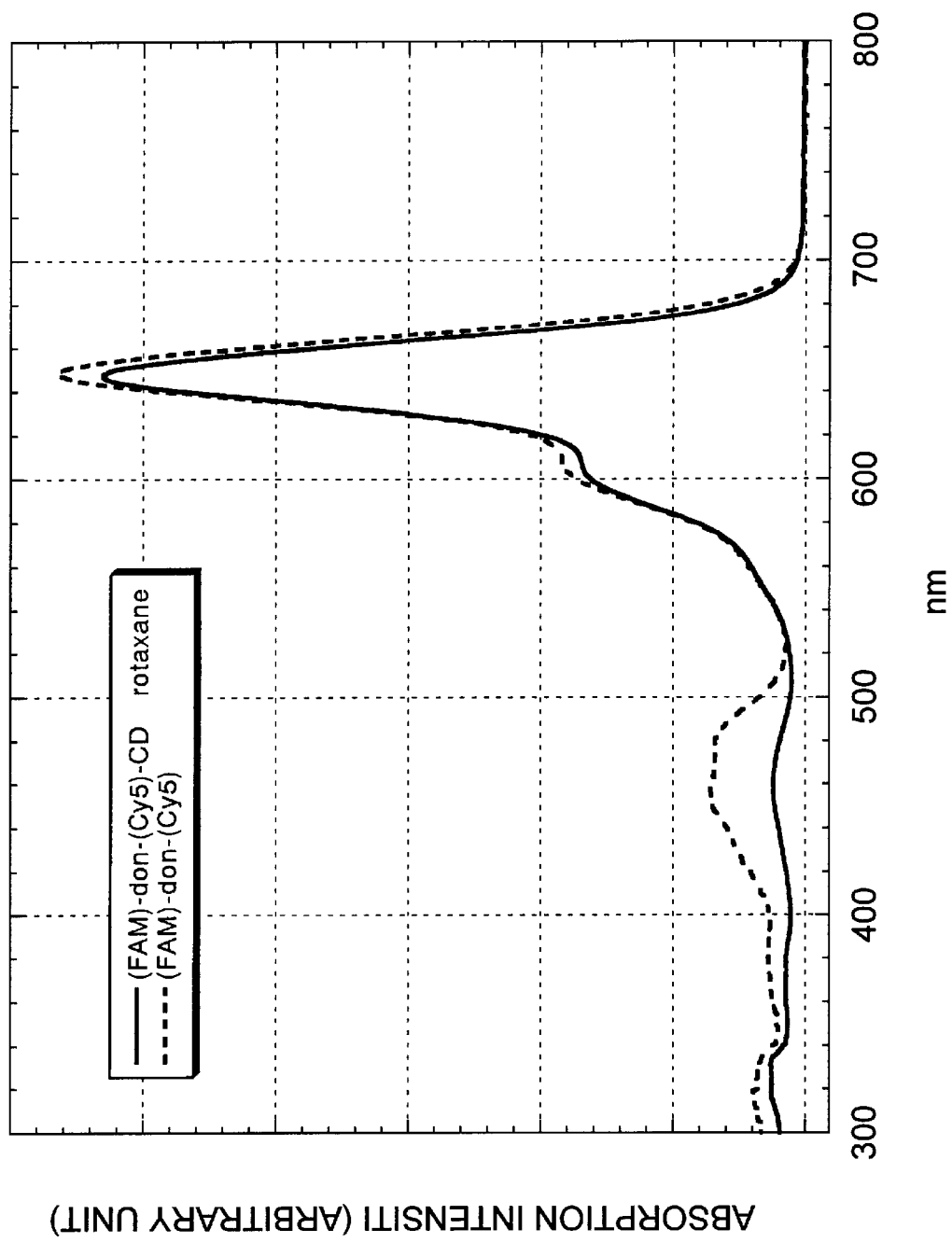
FIG. 20 is a graph showing the absorption spectra of (FAM)-don-(Cy5)-CD rotaxane and (FAM)-don-(Cy5) in methanol/water (1:1) (at concentrations of $1.0\times10^{-6}$ M).
Figure 21:
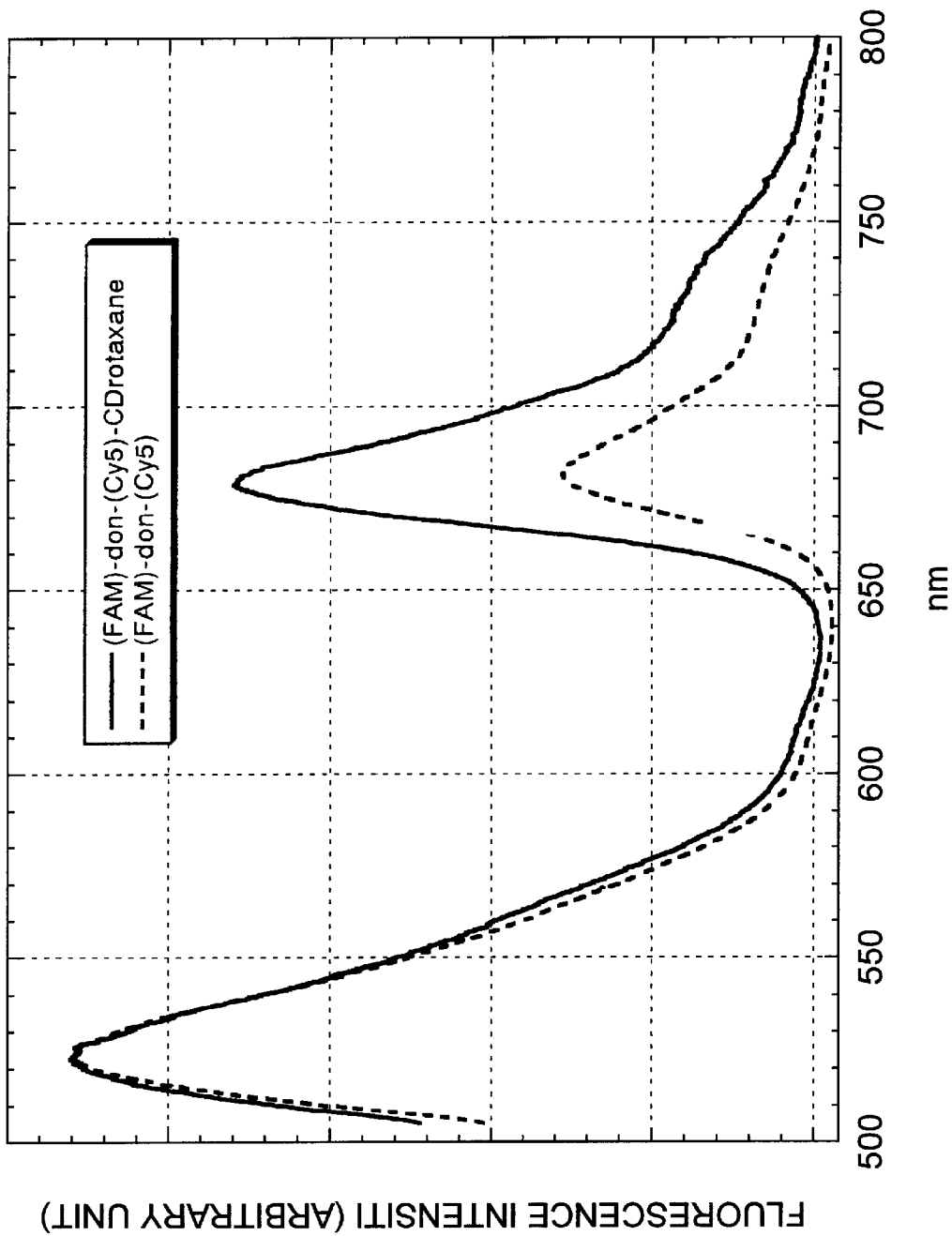
FIG. 21 is a graph showing the fluorescence spectra of (FAM)-don-(Cy5)-CD rotaxane and (FAM)-don-(Cy5) in methanol/water (1:1).

Synthesis of (FAM)-don-(Cy5)-CD Rotaxane (FAM)-don (7.6 mg, 13.6 μmol) was dissolved in 400 μl of an aqueous solution saturated with α-cyclodextrin (α-CD) and upon stirring at 40° C. for 2 days, it was allowed to be included by the CD. To this was added Cy5-OSu(5 mg, 6.6 μmol; available from Amersham Inc.) dissolved in 200 μl of DMF and it was stirred for an additional day. The reaction solution was fractionated based on molecular weights using a gel filtration column. The initially eluted components were a mixture of (FAM)-don-(Cy5)-CD rotaxane and (FAM)-don-(Cy5), so the two components were further separated by reverse phase column chromatography. Two peaks appeared at 5.3 and 20.6 min: the 5.3 min was (FAM)-don-(Cy5)-CD rotaxane and the 20.6 min was (FAM)-don-(Cy5). The 5.3 min component was fractionated and lyophilized.
Analytical HPLC Apparatus and Analytical Conditions:
  Device: Tosoh HPLC system
  Detection: Hitachi ultraviolet and visible photometric detector L-7420 (495 nm); and Hitachi fluorescence detector L-7480 (excitation at 495 nm, emission at 670 nm)
  Column: AsahipackODP-50 4E 4.6 mm×250 mm
  Eluant: gradient of from 50% water (10 mM ammonium acetate)/50% methanol (10 mM ammonium acetate) to 100% methanol (10 mM ammonium acetate)
  Flow rate: 0.6 ml/min
Mass Spectrometry:
  Matrix: DHBA
Absorption and Fluorescence Spectral Measurement:
  in 50% methanol; and excitation wavelength at 495 nm
IR Spectral Analysis (film method):
IR Cards Type 61 Polyethylene 19 mm Aperture available from 3M Inc.
Analytical Results:
  HPLC: retention time of 5.3 min
  TOF-MS: [M+1]+: 2175
  Absorption spectrum: FIG. 20
  Fluorescence spectrum: FIG. 21
  IR spectrum: FIG. 18

EXAMPLE 9

Synthesis of (FAM)-don-(Cy5)

(FAM)-don (7.6 mg, 13.6 μmol) was dissolved in 400 μl of DMF and it was stirred at 40° C. for 2 days. To this was added Cy5-OSu(5 mg, 6.6 μmol; available from Amersham Inc.) dissolved in 200 µl of DMF and it was stirred for an additional day. The reaction solution was fractionated based on molecular weights using a gel filtration column. The initially eluted components were a mixture of (FAM)-don-(Cy5)-CD rotaxane and (FAM)-don-(Cy5), so the two components were further separated by reverse phase column chromatography. Two peaks appeared at 5.3 and 20.6 min: the 5.3 min was (FAM)-don-(Cy5)-CD rotaxane and the 20.6 min was (FAM)-don-(Cy5). The 20.6 min component was fractionated and lyophilized.

Analytical HPLC Apparatus and Analytical Conditions:
  Device: Tosoh HPLC system
  Detection: Hitachi ultraviolet and visible photometric detector L-7420 (495 nm); and Hitachi fluorescence detector L-7480 (excitation at 495 nm, emission at 670 nm)
  Column: AsahipackODP-50 4E 4.6 mm×250 mm
  Eluant: gradient of from 50% water (10 mM ammonium acetate)/50% methanol (10 mM ammonium acetate) to 100% methanol (10 mM ammonium acetate)
  Flow rate: 0.6 ml/min Mass Spectrometry:
  Matrix: DHBA Absorption and Fluorescence Spectral Measurement:
  in 50% methanol; and excitation wavelength at 495 nm IR Spectral Analysis (film method):
  IR Cards Type 61 Polyethylene 19 mm Aperture available from 3M Inc.

Figure 19:
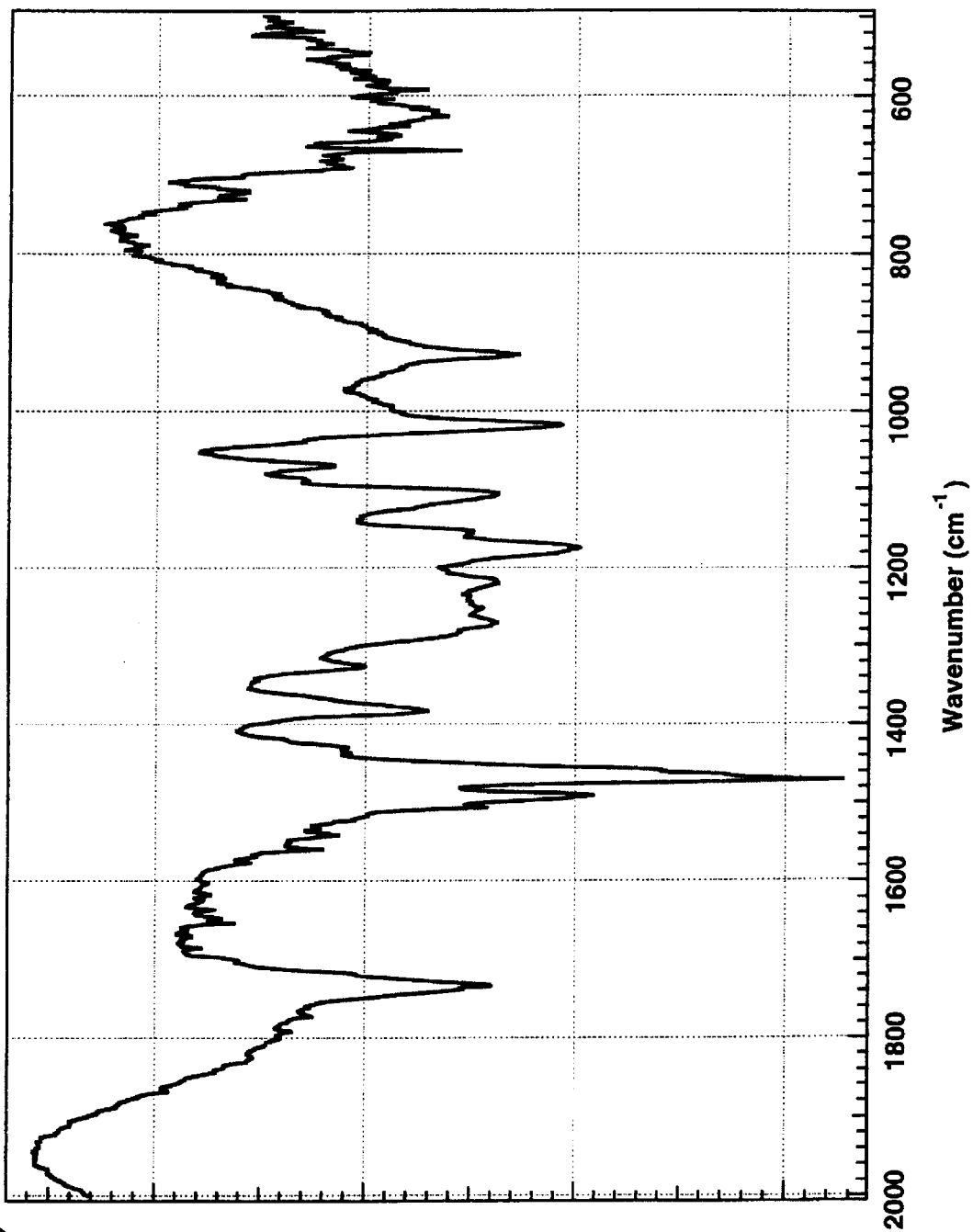
FIG. 19 is a graph showing the infrared absorption spectrum of (FAM)-don-(Cy5).

Analytical Results:
  HPLC: retention time of 20.6 min
  Mass spectrum: [M+1]+: 1199
  Absorption spectrum: FIG. 20
  Fluorescence spectrum: FIG. 21
  IR spectrum: FIG. 19

EXAMPLE 10

Synthesis of Ts-α-CD

Pyridine, 500 ml, and α-CD, 62 g (66 mmol), were taken under a nitrogen atmosphere and while stirring at room temperature, to this was added p-toluenesulfonic acid hydrochloride (39.4 g, 210 mmol) in several portions. Being intact, it was stirred at room temperature overnight, and then, solvent was removed under reduced pressure to afford a syrupy crude reaction product. With respect to this crude reaction product, four peaks were noted in its HPLC analysis: the first peak corresponded to excess p-toluenesulfonic acid and the last peak to unreacted α-CD. This crude reaction product was purified by preparative HPLC. Acetonitrile was removed, under reduced pressure, from the fractions in which the component corresponding to Peak 3—the major product—had been eluted, and then, the residual aqueous solution was lyophilized to afford 13.8 g of mono-(6-tosyl-6-deoxy)-α-cyclodextrin (Ts-α-CD) as a white powder (27% yield).

Analytical HPLC:
  Device: Shimadzu LC-64
  Detection: differential refractometer RID-64
  Column: Kaiseisorb LC-NH$_2$ Super 6 mmφ×250 mm
  Eluant: 60% acetonitrile
  Flow rate: 1.0 ml/min Preparative HPLC:
  Column: 40 mmφ×1000 mm
  Packing Material: NH-DU 3050 available from Fuji Chemicals Co. Ltd.
  Eluant: 60% acetonitrile
  Flow rate: 30 ml/min

EXAMPLE 11

Synthesis of N3-α-CD

Ts-α-CD (0.34 g, 0.45 mmol) and sodium azide (0.32 g, 4.9 mmol) were dissolved in 10 ml of water and it was heated at 80° C. while stirring. After stirring for 4 h, reaction was determined to be over as the disappearance of Ts-α-CD, the starting material, was confirmed. Solvent was removed and precipitation with acetone afforded 0.06 g of N$_3$-α-CD (16% yield).

TLC Analytical Conditions:
  TLC: MERCK.HPTLC-Fertigplatten NH$_2$
  Developing solvent: 60% acetonitrile
  Detection: diphenylamine/aniline/phosphoric acid/acetone 2:2:15:100
  RF value: 0.49

EXAMPLE 12

Synthesis of NH2-α-CD

N$_3$-α-CD (0.50 g, 0.52 mmol) was dissolved in 20 ml of water. To this was added palladium carbon, 40 mg, and a hydrogen gas was passed into it at room temperature for 3 h. The reaction solution turned positive in the ninhydrin coloring. Catalyst was removed by filtration under reduced pressure, the filtrate was concentrated under reduced pressure, and precipitation with acetone afforded 0.41 g of NH$_2$-α-CD (80.8% yield).

TLC Analytical Conditions:
  TLC: MERCK.HPTLC-Fertigplatten NH$_2$
  Developing solvent: 60% acetonitrile
  Detection: diphenylamine/aniline/phosphoric acid/acetone 2:2:15:100
  RF value: 0.43
  TLC: MERCK.Kieselgel 60 F254
  Detection: ninhydrin coloring Conditions for Mass Spectrometric Analysis:
  Matrix: DHBA (Gentistic acid)
  [M−1+Na]+: 994

EXAMPLE 13

Synthesis of Mono-t-butyl Glutarate

Glutaric acid anhydride (5.0 g, 44 mmol) and dimethylaminopyridine (5.4 g, 44 mmol) were dissolved in 70 ml of dichloromethane. To this, under cooling at 0° C., was added t-butyl alcohol (3.3 g, 44 mmol). Being intact, stirring continued at room temperature overnight, and then, a majority of methylene chloride was recovered and 100 ml of water was added. The aqueous phase was acidified with citric acid and extracted with ethyl acetate. After the organic phase was washed with saturated brine and dried over anhydrous sodium sulfate, solvent was removed to afford 3.3 g of the t-butyl ester (yield: 40%).

EXAMPLE 14

Synthesis of Mono-t-butylglutaric Acid Succinimidyl Carbonate

Mono-t-butyl glutarate (3.2 g, 17 mmol), N-hydroxysuccinic acid (2.9 g, 25 mmol), dimethylaminopyridine (0.2 g, 1.7 mmol) and N-ethyl-N-(N,N-dimethyl-3-aminopropyl)-carbodiimide hydrochloride (4.9 g, 26 mmol) were dissolved in 80 ml of dichloromethane. Stirring continued at room temperature overnight. Ordinary aftertreatment was carried out to afford 2.2 g of the desired product as a white crystal (yield: 46%).

EXAMPLE 15

Synthesis of α-Cyclodextrin Glutaramide (CDcooh)

To $NH_2$-α-CD (2.17 g, 2 mmol) dissolved in 40 ml of DMF was added t-butyl-succinimidyl glutarate (0.68 g, 2.4 mmol) and it was stirred at room temperature for 2 days. The reaction solution, being intact, was purified by aminopropylated silica gel column chromatography using 60% acetonitrile as eluant, which resulted in 0.31 g of the desired product. This was dissolved in 5 ml of 1N hydrochloric acid. After stirring at room temperature overnight, it was lyophilized to afford 105 mg of the desired product (yield: 11.3%).

Preparative Chromatographic Conditions:
  Column: 40 mmφ×1000 mm
  Packing Material: NH-DU 3050 available from Fuji Chemicals Co. Ltd.
  Eluant: 60% acetonitrile

EXAMPLE 16

Synthesis of (FAM)-don-(TAMRA)-CDcooh Rotaxane (FAM)-don (7.8 mg, 13.6 μmol) and CDcooh (0.15 g, 70 μmol) were stirred in 1.2 ml of phosphoric acid buffer (pH 9.0) at room temperature overnight. To this added 5-TAMRA, SE (5 mg, 6.6 μmol) dissolved in 200 μl of DMF and it was stirred for an additional day. The reaction solution was fractionated based on molecular weights using a gel filtration column. Mass spectrometric analysis could ascertain that the initially eluted component was (FAM)-don-(TAMRA)-CDcooh rotaxane. Removal of the solvent from the eluted component and drying afforded red powders.

Figure 22:
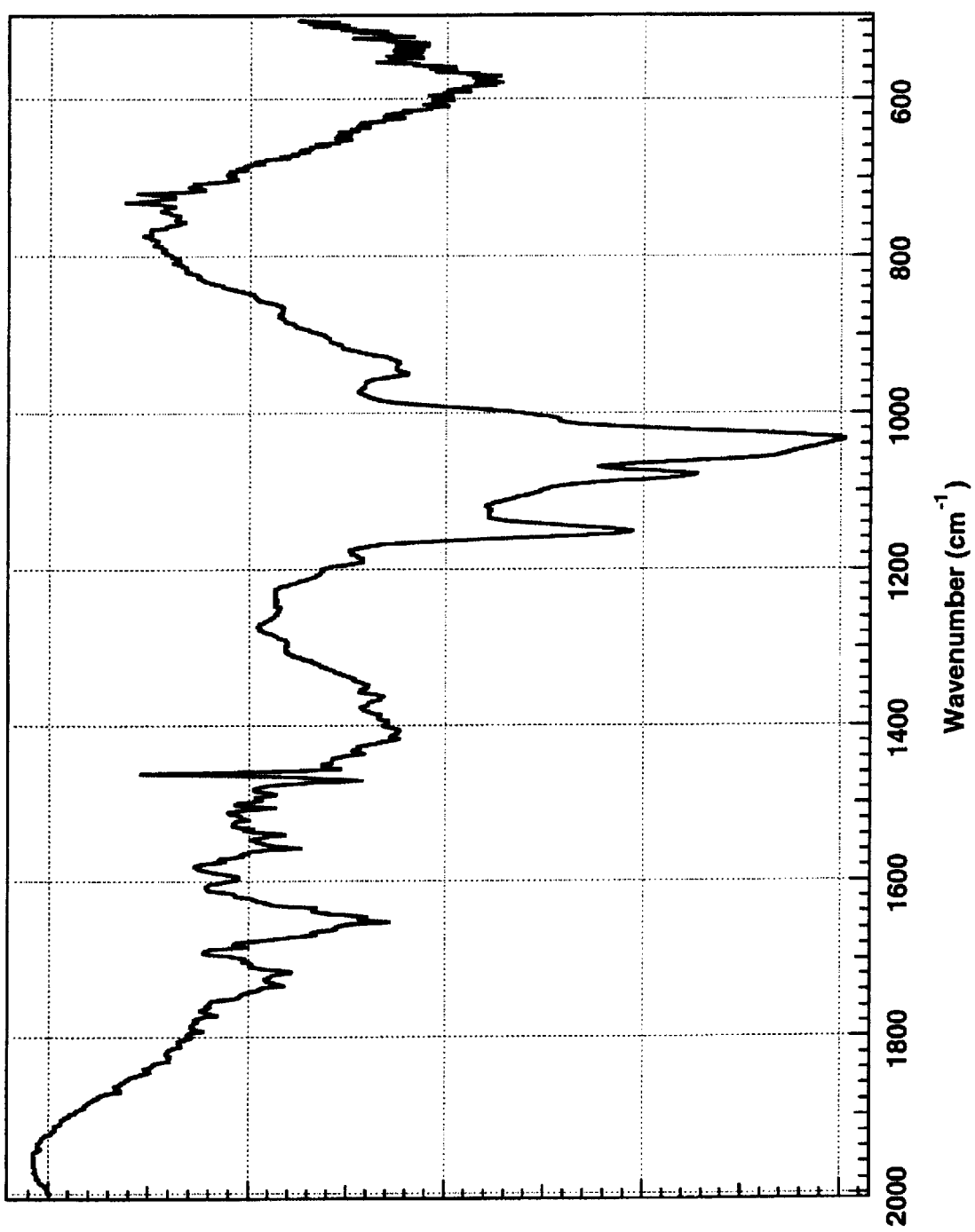
FIG. 22 is a graph showing the infrared absorption spectrum of (FAM)-don-(Cy5)-CDcooh rotaxane.

Analytical HPLC Apparatus and Analytical Conditions:
  Device: Tosoh HPLC system
  Detection: Hitachi ultraviolet and visible photometric detector L-7420 (495 nm); and Hitachi fluorescence detector L-7480 (excitation at 495 nm, emission at 580 nm)
  Column: AsahipackODP-50 4E 4.6 mm×250 mm
  Eluant: gradient of from 50% water (10 mM ammonium acetate)/50% methanol (10 mM ammonium acetate) to 100% methanol (10 mM ammonium acetate)
  Flow rate: 0.6 ml/min
Mass Spectrometry:
  Matrix: DHBA
IR Spectral Analysis (film method):
  IR Cards Type 61 Polyethylene 19 mm Aperture available from 3M Inc.
Analytical Results:
  HPLC: retention time of 5.3 min
  Mass spectrum: [M+1]+2059
  IR spectrum: FIG. 22

EXAMPLE 17

Labeling of Phenetylamine (FAM)-don-(TAMRA)-CDcooh Rotaxane, 3.0 nmol, was dissolved in 90 μl of DMF. To this was added 6 μl of a 10 mM phenetylamine DMF solution (30 nmol: 10-fold quantity of the dye) and 6 μl of a 10 mM dicyclohexylcarbodiimide DMF solution and stirring continued in a dark place at 40° C. for 2 days. HPLC revealed a new peak at 39.3 min, and from the mass spectrum, it was confirmed to be phenetylamine labeled with rotaxane.

Analytical HPLC Apparatus and Analytical Conditions:
  Device: Tosoh HPLC system
  Detection: Hitachi ultraviolet and visible photometric detector L-7424 (546 nm); and Hitachi fluorescence detector L-7480 (excitation at 495 nm, emission at 580 nm)
  Column: AsahipackODP-50 4E 4.6 mm×250 mm
  Eluant: gradient of from 20% water (10 mM ammonium acetate)/80% methanol (10 mM ammonium acetate) to 100% methanol (10 mM ammonium acetate)
  Flow rate: 0.6 ml/min
Mass Spectrometry:
  Matrix: DHBA
Analytical Results:
  HPLC: retention time of 39.3 min
  TOF-MS: [M]+2069

EXAMPLE 18

Measurement of Fluorescence Lifetime of Respective Dyes

The fluorescence lifetime of FAM alone, which is used as donor, is 9.4 ns and it is a lifetime when no energy transfer is involved. With respect to the system where an acceptor dye is present, the fluorescence lifetime of FAM turns out to be about 0.3 ns in cases of B-1 and B-2, whereas it turns out to be about 0.2 ns in cases of C-1 and C-2. It is thus understood that in either case the energy transfer occurs with efficiency of not less than 95%. This can also be ascertained by the fact that there is a rise of the acceptor dye (denoted as "(r)" in the table). The component of an acceptor dye consists of two parts: this is because there are a rise part resulting from excitation by the energy transfer and a part resulting from the fluorescence lifetime of the acceptor dye itself.

When comparisons are made between A-1 and A-2, B-1 and B-2, and C-1 and C-2, problems such as quenching of the acceptor dye caused by the formation of rotaxane derivatives are not noted at all. Thus, the formation of rotaxane derivatives enables the obtaining of dyes that are highly water-soluble and that are capable of multiple coloration.

| | fluorescence lifetime (ns) | | |
|---|---|---|---|
| FAM-don | | 9.4 | |
| TAMRA-don | | 5.1 | |
| A-1 | | 2.7 | |
| A-2 | | 4.2 | |
| B-1 | (FAM) | 0.29 | 3.1 |
| | (TAMRA) | 0.07(r) | 3.0 |
| B-2 | (FAM) | 0.28 | 2.8 |
| | (TAMRA) | 0.08(r) | 3.5 |
| C-1 | (FAM) | 0.21 | 3.9 |
| | (Cy5) | 0.14(r) | 2.3 |
| C-2 | (FAM) | 0.2 | 3.6 |
| | (Cy5) | 0.40(r) | 2.4 |

EXAMPLE 19

Synthesis of TAMRA-don 1,12-Diaminododecane (don) (84.5 mg, 420 μmol) was completely dissolved in 1.8 ml of methanol. To this was added 5-carboxytetramethyl Rhodamine succinimidyl ester (5-TAMRA, SE) (10 mg, 20 μmol) dissolved in 400 μl of DMF dropwise in small amounts. After the dropwise addition was over, stirring continued at 40° C. overnight. The reaction solution was analyzed by HPLC, which ascertained that the 23.3 min was the desired substance. Then, fractionation and purification was done using preparative HPLC. After solvent was removed under reduced pressure from the fractions that had eluted TAMRA-don, the desired component, the residual aqueous solution was lyophilized to afford 8.4 mg of red powders (60% yield).

Analytical HPLC Apparatus and Analytical Conditions:
  Device: Tosoh HPLC system
  Detection: Hitachi ultraviolet and visible photometric detector L-7420 (546 nm); and Hitachi fluorescence detector L-7480 (excitation at 546 nm, emission at 630 nm)
  Column: AsahipackODP-50 4E 4.6 mm×250 mm
  Eluant: gradient of from 50% water (10 mM ammonium acetate)/50% methanol (10 mM ammonium acetate) to 100% methanol (10 mM ammonium acetate)
  Flow rate: 0.6 ml/min
Conditions for Mass Spectrometric Analysis:
  Sample: A 10 μM 50% methanol solution was prepared.
  Matrix: DHBA
Analytical Results:
  HPLC: retention time of 23.3 min
  TOF-MS: [M+1]+: 613

EXAMPLE 20

Synthesis of (TAMRA)-don-CD-ML

To a mixed solution of 0.05 M α-CD aqueous solution, 0.6 ml, and 0.05 M α-CD DMF solution, 2.4 ml, was dissolved TAMRA-don obtained according to the above-mentioned method (10.9 mg, 17.8 μmol) and upon stirring in a dark place at room temperature for 2 days, TAMRA-don was allowed to be included by the CD. After the inclusion, GMBS (50 mg, 178 μmol; available from Dojin Chemicals Co. Ltd.) dissolved in 200 μl of DMF was added and stirring continued at room temperature for an additional day. Unreacted materials of low molecular weight were removed by HPLC and drying was carried out by lyophilization.

Analytical HPLC Apparatus and Analytical Conditions:
  Device: Tosoh HPLC system
  Detection: Hitachi ultraviolet and visible photometric detector L-7420 (546 nm); and Hitachi fluorescence detector L-7480 (excitation at 546 nm, emission at 630 nm)
  Column: YMC-Pack Diol-60
  Eluant: 50% water (10 mM ammonium acetate)/50% methanol (10 mM ammonium acetate)
  Flow rate: 1.0 ml/min
Separation Results:
  Retention time: 13.8 min

EXAMPLE 21

Labeling of GSH with TAMRA-don-CD-ML

Reductive glutathione (GSH), a low molecular weight peptide, was selected as a SH compound and labeling reaction was carried out: GSH stands for Glu-Cys-Gly.

GSH, 50 nmol, was dissolved in 25 μl of phosphoric acid buffer (pH 7.5). To the above-mentioned solution was added TAMRA-don-CD-ML, 100 nmol, dissolved in 100 μl of 20% acetonitrile. Stirring continued in a dark place at room temperature overnight. HPLC analysis revealed a new peak at 5.7 min, and from the mass spectral analysis of the component, it was confirmed to be the dye-labeled GSH.

Analytical HPLC Apparatus and Analytical Conditions:
  Device: Tosoh HPLC system
  Detection: Hitachi ultraviolet and visible photometric detector L-7420 (546 nm); and Hitachi fluorescence detector L-7480 (excitation at 546 nm, emission at 630 nm)
  Column: AsahipackODP-50 4E 4.6 mm×250 mm
  Eluant: gradient of 40% acetonitrile (0.1% TFA) to 80% acetonitrile (0.1% TFA)
  Flow rate: 0.6 ml/min
Conditions for Mass Spectrometric Analysis:
  Sample: A 10 μM 50% acetonitrile solution was prepared.
  Matrix: CHCA
Analytical Results:
  HPLC: retention time of 5.7 min TOF-MS: [M]+2059

EXAMPLE 22

Labeling of Biologically Active Peptide (Gly-Cys-Glu-Tyr-Tyr-Lys-Lys)

Peptide, 150 nmol, was dissolved in 25 μl of phosphoric acid buffer (pH 7.5). To the above-mentioned solution was added TAMRA-don-CD-ML, 75 μmol, dissolved in 125 μl of 20% acetonitrile. Stirring continued in a dark place at room temperature overnight. HPLC analysis revealed a new peak at 6.6 min, and from the mass spectral analysis of the component, it was confirmed to be the dye-labeled peptide.

Analytical HPLC Apparatus and Analytical Conditions:
  Device: Tosoh HPLC system
  Detection: Hitachi ultraviolet and visible photometric detector L-7420 (546 nm); and Hitachi fluorescence detector L-7480 (excitation at 546 nm, emission at 630 nm)
  Column: AsahipackODP-50 4E 4.6 mm×250 mm
  Eluant: gradient of 20% acetonitrile (0.1% TFA) to 80% acetonitrile (0.1% TFA)
  Flow rate: 0.6 ml/min
Conditions for Mass Spectrometric Analysis:
  Sample: A 10 μM 50% acetonitrile solution was prepared.
  Matrix: CHCA
Analytical Results:
  HPLC: retention time of 6.6 min
  TOF-MS: [M+Matrix]+2830

EXAMPLE 23

Labeling of Biologically Active Peptide (Gly-Cys-Asp-Arg-Val-Ile-His-Pro-Phe(C-Ang))

Peptide, 250 nmol, was dissolved in 25 μl of phosphoric acid buffer (pH 7.5). To the above-mentioned solution was added TAMRA-don-CD-ML, 125 μmol, dissolved in 125 μl of 20% acetonitrile. Stirring continued in a dark place at room temperature overnight. HPLC analysis revealed a new peak at 6.0 min, and from the mass spectral analysis of the component, it was confirmed to be the dye-labeled peptide.

Analytical HPLC Apparatus and Analytical Conditions:
  Device: Tosoh HPLC system
  Detection: Hitachi ultraviolet and visible photometric detector L-7420 (546 nm); and Hitachi fluorescence detector L-7480 (excitation at 546 nm, emission at 630 nm)
  Column: AsahipackODP-50 4E 4.6 mm×250 mm
  Eluant: gradient of 40% acetonitrile (0.1% TFA) to 80% acetonitrile (0.1% TFA)
  Flow rate: 0.6 ml/min
Conditions for Mass Spectrometric Analysis:
  Sample: A 10 μM 50% acetonitrile solution was prepared.
  Matrix: CHCA
Analytical Results:
  HPLC: retention time of 6.0 min
  TOF-MS: [M+Matrix]+3151

EXAMPLE 24

Labeling of BSA

Bovine serum albumin (BSA), a high molecular weight protein, was labeled. Mass spectroscopy or the like ascertained that one molecule of SBA was bound to one molecule of dye.

TAMRA-don-CD-ML, 50 nmol, was dissolved in a mixed solution of 400 μl of phosphoric acid buffer (pH 7.5) and 50 μl of DMF. To this was added 99 μl (30-fold quantity of the dye) of a 1% BSA aqueous solution (pH 7.5 phosphoric acid buffer plus 5 mM EDTA) and it was allowed to stand at 4° C. overnight. The high molecular weight component was separated from the low molecular weight component (non-bonded dye) by means of Sephadex G-25. HPLC analysis of the fractionated high molecular weight component revealed a new peak at 7.8 min, and from the mass spectral analysis of the component, it was in agreement with the molecular weight of the dye-labeled BSA.

Analytical HPLC Apparatus and Analytical Conditions:
  Device: Tosoh HPLC system
  Detection: Hitachi ultraviolet and visible photometric detector L-7420 (546 nm); and Hitachi fluorescence detector L-7480 (excitation at 546 nm, emission at 630 nm)
  Column: TSKgel G3000SW$_{XL}$
  Eluant: 50 mM phosphoric acid buffer+0.3 M NaCl
  Flow rate: 1.0 ml/min
Conditions for Mass Spectrometric Analysis:
  Matrix: SA (Sinapinic acid)
Analytical Results:
  HPLC: retention time of 8.6 min
  TOF-MS: [M]+67315

2. A rotaxane-type dye represented by the following formula 2:

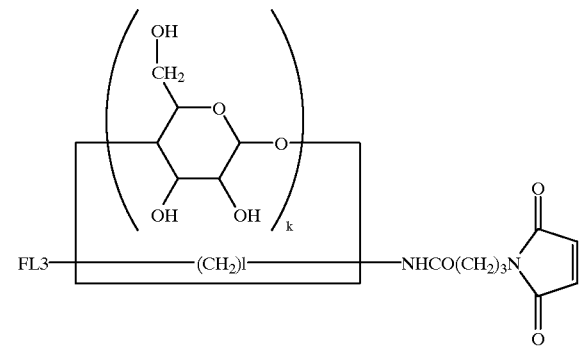

(Formula 2)

wherein FL3 represents a dye; k represents an integer of 6–8; and l represents an integer of 8–12.

3. The rotaxane type dye of claim 1, wherein the dye is a fluorescent dye.

4. The rotaxane type dye of claim 2, wherein the dye is a fluorescent dye.

What is claimed is:

1. A rotaxane-type dye represented by the following formula 1:

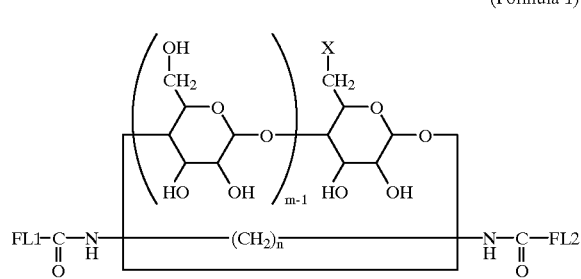

(Formula 1)

wherein each of FL1 and FL2 represents a dye; n represents an integer of 8–12; m represents an integer of 6–8; and X is selected from the group consisting of OH, Cl, Br, I, NH$_2$, NCO, NHCO, and (CH$_2$)$_3$CO$_2$H.

5. A labeling agent comprising a rotaxane-type dye represented by the following formula 1:

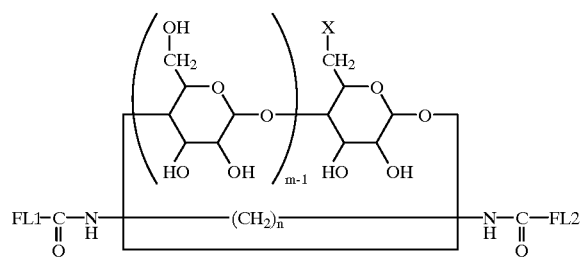

(Formula 1)

wherein each of FL1 and FL2 represents a dye; n represents an integer of 8–12; m represents an integer of 6–8; and X is selected from the group consisting of OH, Cl, Br, I, NH$_2$, NCO, NHCO, and (CH$_2$)$_3$CO$_2$H; and into which a labeling reactive group has been introduced.

6. A labeling agent comprising the dye of claim 2 into which a labeling reactive group has been introduced.

7. A labeling agent comprising a rotaxane-type dye represented by the following formula 1:

(Formula 1)

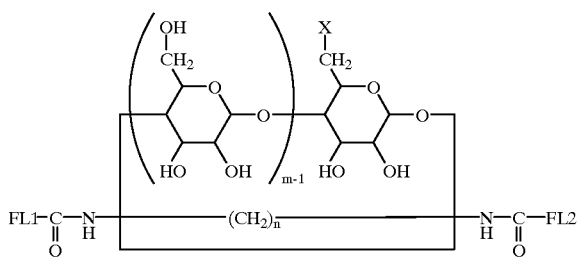

wherein each of FL1 and FL2 represents a dye; n represents an integer of 8–12; m represents an integer of 6–8; and X is selected from the group consisting of OH, Cl, Br, I, $NH_2$, NCO, NHCO, and $(CH_2)_3CO_2H$, and further;

wherein the dye is a fluorescent dye, and into which a labeling reactive group has been introduced.

8. A labeling agent comprising the dye of claim 4 into which a labeling reactive group has been introduced.

9. A labeling method comprising the use of the labeling agent of claim 5 to label a substance.

10. A labeling method comprising the use of the labeling agent of claim 6 to label a substance.

11. A labeling method comprising the use of the labeling agent of claim 7 to label a substance.

12. A labeling method comprising the use of the labeling agent of claim 8 to label a substance.

* * * * *